(12) United States Patent
Prestrelski et al.

(10) Patent No.: US 10,765,683 B2
(45) Date of Patent: *Sep. 8, 2020

(54) STABLE FORMULATIONS FOR PARENTERAL INJECTION OF SMALL MOLECULE DRUGS

(71) Applicant: Xeris Pharmaceuticals, Inc., Chicago, IL (US)

(72) Inventors: Steven J. Prestrelski, San Diego, CA (US); Nancy Scott, Chicago, IL (US)

(73) Assignee: Xeris Pharmaceuticals, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/812,515

(22) Filed: Jul. 29, 2015

(65) Prior Publication Data

US 2016/0151385 A1 Jun. 2, 2016

Related U.S. Application Data

(63) Continuation of application No. 13/829,937, filed on Mar. 14, 2013, now Pat. No. 9,125,805.

(60) Provisional application No. 61/665,021, filed on Jun. 27, 2012.

(51) Int. Cl.

| | |
|---|---|
| *A61K 31/5513* | (2006.01) |
| *A61K 47/20* | (2006.01) |
| *A61K 47/22* | (2006.01) |
| *A61K 9/00* | (2006.01) |
| *A61K 9/08* | (2006.01) |
| *A61K 47/14* | (2017.01) |
| *A61K 47/10* | (2017.01) |
| *A61K 31/137* | (2006.01) |
| *A61K 31/167* | (2006.01) |
| *A61K 31/352* | (2006.01) |
| *A61K 31/4045* | (2006.01) |
| *A61K 31/4196* | (2006.01) |
| *A61K 31/496* | (2006.01) |
| *A61K 31/55* | (2006.01) |
| *A61K 31/675* | (2006.01) |
| *A61K 31/7036* | (2006.01) |

(52) U.S. Cl.
CPC ........ *A61K 31/5513* (2013.01); *A61K 9/0019* (2013.01); *A61K 9/08* (2013.01); *A61K 31/137* (2013.01); *A61K 31/167* (2013.01); *A61K 31/352* (2013.01); *A61K 31/4045* (2013.01); *A61K 31/4196* (2013.01); *A61K 31/496* (2013.01); *A61K 31/55* (2013.01); *A61K 31/675* (2013.01); *A61K 31/7036* (2013.01); *A61K 47/10* (2013.01); *A61K 47/14* (2013.01); *A61K 47/20* (2013.01); *A61K 47/22* (2013.01)

(58) Field of Classification Search
CPC .. A61K 31/5513; A61K 9/0019; A61K 47/20; A61K 47/22; A61K 9/08

USPC ........................................................ 514/221
See application file for complete search history.

(56) References Cited

U.S. PATENT DOCUMENTS

| | | | |
|---|---|---|---|
| 3,016,895 A | 1/1962 | Sein | 604/60 |
| 4,272,548 A | 6/1981 | Gatzen et al. | |
| 4,608,764 A | 9/1986 | Leuenberger | 34/295 |
| 4,848,094 A | 7/1989 | Davis et al. | 62/64 |
| 4,927,571 A | 5/1990 | Huang et al. | 264/4.3 |
| 5,031,336 A | 7/1991 | Diesner et al. | 34/287 |
| 5,092,843 A | 3/1992 | Monroe et al. | 604/138 |
| 5,208,998 A | 5/1993 | Oyler | 34/288 |
| 5,260,306 A | 11/1993 | Boardman et al. | 514/291 |
| 5,397,771 A | 3/1995 | Bechgaard et al. | |
| 5,716,640 A | 2/1998 | Kamei et al. | 524/451 |
| 5,932,547 A | 8/1999 | Stevenson et al. | 514/10.3 |
| 5,977,082 A | 11/1999 | Gatti et al. | 514/34 |
| 6,001,336 A | 12/1999 | Gordon | 424/46 |
| 6,051,256 A | 4/2000 | Platz et al. | 424/489 |
| 6,124,261 A | 9/2000 | Stevenson et al. | 514/2.4 |
| 6,199,297 B1 | 3/2001 | Wisniewski | 34/284 |
| 6,253,463 B1 | 7/2001 | Hansen | 34/362 |
| 6,264,990 B1 | 7/2001 | Knepp et al. | 424/499 |
| 6,290,991 B1 | 9/2001 | Roser et al. | 424/502 |
| 6,309,663 B1 | 10/2001 | Patel et al. | 424/450 |
| 6,331,310 B1 | 12/2001 | Roser et al. | 424/423 |
| 6,365,637 B1 | 4/2002 | Zirnstein et al. | |
| 6,371,939 B2 | 4/2002 | Bergens et al. | 604/156 |
| 6,495,164 B1 | 12/2002 | Ramstack et al. | 424/489 |

(Continued)

FOREIGN PATENT DOCUMENTS

| | | |
|---|---|---|
| CN | 1507858 | 6/2004 |
| CN | 1582170 | 2/2005 |

(Continued)

OTHER PUBLICATIONS

Griebel et al. SL651498, a GABAA Receptor Agonist with Subtype-Selective Efficacy, as a Potential Treatment for Generalized Anxiety Disorder and Muscle Spasms. CNS Drug Reviews vol. 9, No. 1, pp. 3-20, 2003.*

(Continued)

*Primary Examiner* — Yih-Horng Shiao (74) *Attorney, Agent, or Firm* — Sterne, Kessler, Goldstein & Fox P.L.L.C.

(57) ABSTRACT

Disclosed is a stable liquid formulation for parenteral injection comprising a biocompatible non-aqueous solvent and a small molecule drug, or a salt thereof, solubilized within the non-aqueous solvent, wherein the liquid formulation comprises less than 10% by weight residual water, and wherein the volume of the liquid formulation to be parenterally injected is from 0.1 µl to 3 ml.

13 Claims, 1 Drawing Sheet

(56) References Cited

U.S. PATENT DOCUMENTS

| | | | |
|---|---|---|---|
| 6,667,061 B2 | 12/2003 | Ramstack et al. | 424/489 |
| 6,676,958 B2 | 1/2004 | Gerber | 424/434 |
| 6,730,328 B2 | 5/2004 | Maskiewicz et al. | 424/499 |
| 7,005,421 B2 | 2/2006 | Gatti et al. | 514/34 |
| 7,163,704 B2 | 1/2007 | Zhang | 424/725 |
| 7,259,225 B2 | 8/2007 | Song et al. | 528/272 |
| 7,314,636 B2 | 1/2008 | Caseres et al. | 424/426 |
| 7,371,406 B2 | 5/2008 | Rasstack et al. | 424/489 |
| 7,396,841 B2 | 7/2008 | Doen et al. | 514/338 |
| 7,442,832 B2 | 10/2008 | Gentile et al. | 562/460 |
| 7,498,312 B2 | 3/2009 | Cohen et al. | 514/36 |
| 7,582,311 B1 | 9/2009 | Cleland et al. | 424/489 |
| 7,604,822 B2 | 10/2009 | Ionascu | 424/725.1 |
| 7,651,703 B2 | 1/2010 | Cleland et al. | 424/489 |
| 7,915,229 B2 | 3/2011 | Cohen et al. | 514/36 |
| 8,110,209 B2 | 2/2012 | Prestrelski et al. | 424/423 |
| 8,946,208 B2 | 2/2015 | Castile et al. | |
| 9,125,805 B2 * | 9/2015 | Prestrelski | A61K 9/08 |
| 9,138,479 B2 | 9/2015 | Prestrelski et al. | |
| 2002/0179647 A1 | 12/2002 | Hall et al. | 222/175 |
| 2003/0013753 A1 | 1/2003 | Aung-Din | |
| 2003/0026884 A1 | 2/2003 | Mantius et al. | 426/488 |
| 2003/0119825 A1 | 6/2003 | Folger et al. | 514/226.5 |
| 2003/0170289 A1 | 9/2003 | Chen et al. | 424/426 |
| 2003/0191157 A1 | 10/2003 | Doen et al. | 514/337 |
| 2004/0142043 A1 | 7/2004 | Maeda et al. | 524/499 |
| 2004/0176341 A1 | 9/2004 | Chou et al. | 514/179 |
| 2005/0019436 A1 | 1/2005 | Burch et al. | 424/760 |
| 2005/0069591 A1 | 3/2005 | Bernstein et al. | 424/489 |
| 2005/0240166 A1 | 10/2005 | Harper et al. | 604/890.1 |
| 2006/0160823 A1 | 7/2006 | Witchey-Lakshmanan et al. | 514/254.07 |
| 2006/0211982 A1 | 9/2006 | Prestrelski et al. | 604/60 |
| 2007/0196416 A1 | 8/2007 | Li et al. | 424/422 |
| 2008/0096567 A1 | 4/2008 | Lopez et al. | 514/567 |
| 2008/0132493 A1 | 6/2008 | Folger et al. | 514/224.2 |
| 2008/0145383 A1 | 6/2008 | Zauner et al. | 424/208.1 |
| 2008/0160067 A1 | 7/2008 | Boeckh et al. | 424/441 |
| 2008/0200383 A1 | 8/2008 | Jennings et al. | 424/497 |
| 2008/0220069 A1 | 9/2008 | Allison | 424/489 |
| 2008/0226689 A1 | 9/2008 | Berry et al. | 424/423 |
| 2008/0248999 A1 | 10/2008 | Steiner | 514/1.1 |
| 2008/0260840 A1 | 10/2008 | Alessi et al. | 424/489 |
| 2008/0305161 A1 | 12/2008 | Shah et al. | 424/456 |
| 2009/0143737 A1 | 6/2009 | Kobayashi et al. | 604/164.08 |
| 2009/0215883 A1 | 8/2009 | Bouzada et al. | 514/449 |
| 2009/0226689 A1 | 9/2009 | Lassner et al. | 514/12 |
| 2009/0233912 A1 | 9/2009 | Castile et al. | 514/220 |
| 2010/0098735 A1 | 4/2010 | Jain et al. | 424/422 |
| 2010/0120660 A1 | 5/2010 | Balschmidt et al. | 514/1.1 |
| 2011/0230569 A1 | 9/2011 | Nistor et al. | 514/777 |
| 2012/0046225 A1 | 2/2012 | Prestrelski et al. | 514/6.8 |
| 2012/0232001 A1 | 9/2012 | Prestrelski et al. | 514/5.9 |
| 2013/0065886 A1 | 3/2013 | Cart | |
| 2013/0123739 A1 | 5/2013 | Yoshikawa | 604/408 |
| 2013/0317477 A1 | 11/2013 | Edwards et al. | |
| 2014/0058337 A1 | 2/2014 | Claussen et al. | 604/260 |
| 2014/0171362 A1 | 6/2014 | Prestrelski et al. | 514/5.9 |
| 2014/0179599 A1 | 6/2014 | Prestrelski et al. | 514/6.8 |
| 2014/0179600 A1 | 6/2014 | Prestrelski et al. | 514/6.8 |
| 2014/0221288 A1 | 8/2014 | Prestrelski et al. | 514/7.2 |
| 2014/0296191 A1 | 10/2014 | Patel | |
| 2015/0250855 A1 | 9/2015 | Prestrelski et al. | 514/6.8 |
| 2016/0000803 A1 | 1/2016 | Schwarz et al. | |
| 2017/0007675 A1 | 1/2017 | Prestrelski et al. | |
| 2017/0049858 A1 | 2/2017 | Prestrelski et al. | |

FOREIGN PATENT DOCUMENTS

| | | |
|---|---|---|
| CN | 101842079 | 9/2010 |
| CN | 102164579 | 8/2011 |
| CN | 103442695 | 9/2012 |
| EP | 0 916 347 | 5/1999 |
| EP | 0916347 | 5/1999 |
| EP | 1 502 589 | 2/2005 |
| EP | 1502589 | 2/2005 |
| EP | 2030610 | 3/2009 |
| EP | 2 060 268 | 5/2009 |
| EP | 2526996 | 11/2012 |
| GB | 2 119 248 | 11/1983 |
| JP | H07-506287 | 7/1995 |
| JP | H05-507085 | 10/1997 |
| JP | 2006-506363 | 2/2006 |
| JP | 2006-511582 | 4/2006 |
| JP | 2007-537283 | 12/2007 |
| JP | 2008-543857 | 12/2008 |
| JP | 2009-523798 | 6/2009 |
| JP | 2010-537963 | 12/2010 |
| JP | 2010537963 | 12/2010 |
| JP | 2011-507843 | 3/2011 |
| JP | 2011-520875 | 7/2011 |
| JP | 2014-507484 | 3/2014 |
| JP | 2014-510077 | 4/2014 |
| WO | WO 2016/022831 | 2/1916 |
| WO | WO 2016/196976 | 12/1916 |
| WO | WO 2016/201248 | 12/1916 |
| WO | WO 1991/16882 | 11/1991 |
| WO | WO 1994/013344 | 6/1994 |
| WO | WO 1995/32730 | 12/1995 |
| WO | WO 1996/009814 | 4/1996 |
| WO | WO 1998/009613 | 3/1998 |
| WO | WO 1998/016250 | 4/1998 |
| WO | WO 1998/027963 | 7/1998 |
| WO | WO 2000/016829 | 3/2000 |
| WO | WO 2001/076682 | 10/2001 |
| WO | WO 2001/078687 | 10/2001 |
| WO | WO 2002/000137 | 1/2002 |
| WO | WO 2002/049660 | 6/2002 |
| WO | WO 2003/007782 | 1/2003 |
| WO | WO 2003/041684 | 5/2003 |
| WO | WO 2003/051398 | 6/2003 |
| WO | WO03051398 | 6/2003 |
| WO | WO 2004/035601 | 4/2004 |
| WO | WO 2004/037242 | 5/2004 |
| WO | WO 2004/057939 | 7/2004 |
| WO | WO 2004/057959 | 7/2004 |
| WO | WO 2004/091666 | 10/2004 |
| WO | WO 2004/098643 | 11/2004 |
| WO | WO 2005/010079 | 2/2005 |
| WO | WO 2005/021046 | 3/2005 |
| WO | WO 2006/031376 | 3/2006 |
| WO | WO 2006/110551 | 10/2006 |
| WO | WO 2006/122217 | 11/2006 |
| WO | WO 2006/138347 | 12/2006 |
| WO | WO 2007/059019 | 5/2007 |
| WO | WO 2007/140312 | 12/2007 |
| WO | WO 2008/030469 | 3/2008 |
| WO | WO 2008/041245 | 4/2008 |
| WO | WO 2008/098212 | 8/2008 |
| WO | WO 2008/132224 | 11/2008 |
| WO | WO 2009/027697 | 3/2009 |
| WO | WO 2009/045837 | 4/2009 |
| WO | WO 2009/060473 | 5/2009 |
| WO | WO 2009/070298 | 6/2009 |
| WO | WO 2009/082437 | 7/2009 |
| WO | WO 2010/018596 | 2/2010 |
| WO | WO 2010/024209 | 3/2010 |
| WO | WO 2010036702 | 4/2010 |
| WO | WO 2011/060908 | 5/2011 |
| WO | WO 2011/154725 | 12/2011 |
| WO | WO2011154725 | 12/2011 |
| WO | WO 2012/012460 | 1/2012 |
| WO | WO 2012/122535 | 9/2012 |
| WO | WO 2013/067022 | 5/2013 |
| WO | WO 2013/173687 | 11/2013 |
| WO | WO 2014/004895 | 1/2014 |
| WO | WO 2014/036323 | 3/2014 |
| WO | WO 2014/124151 | 8/2014 |

(56) References Cited

FOREIGN PATENT DOCUMENTS

| WO | WO 2015/120231 | 8/2015 |
|---|---|---|
| WO | WO 2015/153728 | 10/2015 |

OTHER PUBLICATIONS

Ellson et al. In situ DMSO hydration measurements of HTS compound libraries. Comb Chem High Throughput Screen. Sep. 2005;8(6):489-98 (Abstract only) (Year: 2005).*

Vanderweele et al., "Glucagon, Satiety From Feeding and Liver/Pancreatic Interactions," Brain Research Bulletin, 17:539-543 (1986).

International Search Report and Written Opinion issued in PCT/US2015/044060, dated Nov. 2, 2015.

International Search Report and Written Opinion issued in PCT/US2015/014756, dated Sep. 25, 2015.

International Search Report and Written Opinion issued in PCT/US2015/023820, dated Jun. 18, 2015.

Administer Intramuscular, Subcutaneous, and Intradermal Injections, from http://www.brooksidepress.org/Products/Administer_IM_SQ_and_ID_Injections/lesson_1 . . . , pp. 1-3, published on 2007.

Anderson et al., "Revised estimate of the prevalence of multiple sclerosis in the United States", Ann. Neruol, 31(3):333-336, 1992.

Arnon and Aharoni, "Neurogenesis and neuroprotection in the CNS—fundamental elements in the effect of Glatiramer acetate on treatment of autoimmune neurological disorders", Mol. Neurobiol., 36:245-253, 2007.

Autret, E. et al.: "Double-blind, randomized trial of diazepam versus placebo for prevention of recurrence of febrile seizures", The Journal of Pediatrics, vol. 117, No. 3, Sep. 1990, p. 490-494.

Bjartmar and Fox, "Pathological mechanisms and disease progression of multiple sclerosis: therapeutic implications", Drugs of Today, 38:17-29, 2002.

Bornstein et al., "A pilot trial of Cop 1 in exacerbateing remitting multiple sclerosis", New Eng. J. Med., 317:408-414,1987.

Bornstein et al., "A placebo-controlled, double-blind, randomized, two-center, pilot trial of Cop-1 in chronic progressive multiple sclerosis", Neurology, 41:533-539, 1991.

Bromberg, L. et al., "Transport of proteins dissolved in organic solvents across biomimetic membranes", Proceedings of the National Academy of Sciences 92(5):1262-1266, 1995.

Buffer Reference Center, from http://sigmaaldrich.com/life-science/core-bioreagents/biological-buffers/learningcenter. Accessed Jul. 3, 2013.

Buffer Reference Center, from http;//www.sigmaaldrich.com/, pp. 1-7, accessed Jul. 3, 2013.

Carpenter, et al., "Rational Design of Stable Lyophilized Protein Formulations: Theory and Practice." pp. 1-25. 2002.

Cervera et al, "Mechanism of action of exenatide to reduce postprandial hyperglycemia in type 2 diabetes", Am. J. Physiol. Endocrinol. Metab., 294:E846-E852, 2008.

Chang and Hershenson, "Practical Approaches to Protein Formulation Development", In: Rationale Design of stable protein formulations—theory and practice, pp. 1-25, 2002.

Chang et al., "Development of a Stable Freeze-dried formulation of Recombinant Human Interleukin-1 Receptor Antagonist", Pharmaceutical Research, 13(2):243-249, 1996.

Comi & Filippi, "Treatment with glatiramer acetate delays conversion to clinically definiate multiple sclerosis (CDMS) in patients with clinically isolated syndromes (CIS)", Neurology, 71(2):153, 2008.

Comi et al, "Results from a phase III, one-year, randomized, double-blind, parallel-group, dosecomparison study with glatiramer acetate in relapsing-remitting multiple sclerosis", Mult. Scler., 14(suppl. 1):S299, 2008.

Comi et al., "European/Canadian multicener, double-blind, randomized, placebo-controlled study of the effects of glatiramer acetate on magnetic resonance imaging-measured disease activity and burden in patents with relapsing multiple sclerosis", Ann. Neurol., 49:290-297, 2001.

Compston et al., "The Story of Multiple Sclerosis" In: McAlpine's Multiple Sclerosis. London: Churchill Livingston, pp. 3-42, 2006.

Definition of analog, from http://cancerweb.ncl.ac.uk/cgi-bin/omd?query=analog, pp. 1-5, accessed Jul. 7, 2005.

Definition of mimetic, from http://www.merriam-webster.com/medical/mimetic, p. 1, accessed Jun. 26, 2014.

DeLuca, "Freeze drying of pharmaceuticals", J. Vac. Sci. Technol., 14(1):620, 1977.

Dhib-Jalbut, "Glatirmaer acetate (Copaxone) therapy for multiple sclerosis", Pharmacol Ther., 98:245-255 2003.

Dhib-Jalbut, "Mechanisms of action of interferons and glatiramer acetate in multiple sclerosis", Neurology, 25 58(Suppl 4): S3-S9, 2002.

Diabetes Mellitus—Merck Manual, from http://www.merckmanuals.com/professional/print!endocrine_and_metabolic_disorders/diab . . . , pp. 1-22, accessed Apr. 2, 2013.

Encyclopedia of Pharmaceutical Technology, vol. 6, Suspensions, pp. 3597-3610, 2007.

European Search Report for EP Appl. No. EP 12180169.0 dated Oct. 25, 2012.

Fleming and Carrithers, "Diagnosis and management of multiple sclerosis", Professional communications, Inc., 4 pages, 2002.

Geary and Smith, "Pancreatic Glucagon Fails to Inhibit Sham Feeding in the Rat", Peptides, 1:163-166, 1982.

Guideline on clinical investigation of medicinal products for the treatment of multiple sclerosis EMEA, London Sep. 16, 2006.

Hypoglycemia—Merck Manual, from http://web.archive.org/web/20120115004118/http://www.merckmanuals.com/professional/ pp. 1-2, published on May 2007.

International Search Report and Written Opinion issued in PCT Application PCT/US2011/044576, dated Dec. 14, 2011.

International Search Report and Written Opinion issued in PCT Application PCT/US2012/028621, dated Aug. 22, 2012.

International Search Report and Written Opinion Issued in PCT Application No. PCT/US2014/015123, dated Apr. 3, 2014.

International Search Report and Written Opinion issued in PCT Application PCT/US2012/062816, dated Jan. 31, 2013.

International Search Report and Written Opinion issued in PCT Application PCT/US2013/048293, dated Aug. 8, 2013.

Johnson et al., "Extended use of glatiramer acetate (Copaxone) is well tolerated and maintains its clinical effect on multiple sclerosis relapse rate and degree of disability", Neurology, 50:701-708, 1998.

Kansara et al., "Subcutaneous delivery", Drug. Deliv. Technol, 9(6):38-42, 2009.

Knudsen, F Ursin; "Recurrence risk after first febrile seizure and effect of short term diazepam prophylaxis", Archives of Disease in Childhood, vol. 60, 1985 p. 1045-1049.

Izutsu, Stabilization of Therapeutic Proteins by Chemical and Physical Methods, pp. 287-292, from Therapeutic Proteins Methods and Protocols, Edited by C. Mark Smales and David C. James, published on 2005.

Meyer et al., "Preparation and in vitro characterization of gentamycin-impregnated biodegradable beads suitable for treatment of osteomyelitis", Journal of Pharmaceutical Sciences, 87(9):1149-1154, 1998.

Noseworthy et al, "Multiple sclerosis", New Engl. J. Med., 343:938-952, 2000.

Pellock, John et al.: Pediatric Epilepsy: Diagnosis and Therapy: Third Edition—Chapter 19 "Febrile Seizures", 2008, p. 293-301.

Rubiono, Solubilization of Some Poorly Soluble Drug by cosolvents, PhD dissertation, The University of Arizona, 1984.

Ruggiere et al., "Glatiramer acetate in multiple sclerosis: A review", CNS Drug Reviews, 13(2):178-191, 2007.

Shire et al., "Challenges in the development of high protein concentration formulations", J. Pharm. Sci., 93(6):1390-1402, 2004.

Tselis et al., "Glatiramer acetate in the treatment of multiple sclerosis", Neuropsychiatric Dis. Treat. 5Q, 3(2):259-267, 2007.

Wang, "Lyophilization and development of solid protein pharmaceuticals", International Journal of Pharmaceutics, 203:1-60, 2000.

(56) References Cited

OTHER PUBLICATIONS

Weber et al., "Mechanism of action of glatiramer acetate in treatment of multiple sclerosis", Neurotherapeutics, 4(4):647-653, 2007.
Williams and Polli, "The lyophilization of pharmaceuticals: a literature review", Journal of Parenteral Science and Technology, 38(2), 1984.
Wolinsky et al, "Glatiramer acetate in primary progressive multiple sclerosis: Results of a multinationa, multicener, double-blind, placebo-controlled trial", Ann Neurool, 61:14-24, 2007.
Wolinsky, "The use of glatiramer acetate in the treatment of multiple sclerosis", Adv. Neurol., pp. 273-292, 2006.
Zacharis et al., "Volatile buffers can override the 'pH memory' of subtilisin catalysis in organic media", Proc. Natl. Acad. Sci. USA, 96:1201-1205, 1999.
Ziemssen and Schrempf, "Glatiramer acetate: Mechanisms of action in multiple sclerosis", International Rev. of Neurobiol., 79:537-570, 2007.
Glossary of medical education terms, institute of International Medical Education. http://www.iime.org/glossary.htm. Accessed in Mar. 2013.
Iasemidis LD, "Epileptic Seizure Prediction and Control." IEEE Transac Biomed Eng. 50:549-558. 2003.
Amylin Agonists, from http://www.globalrph.com/amylin-agonists.htm, pp. 1-5, accessed Nov. 30, 2014.
Brown: "Clinicians' Guide to Diabetes Gadgets and Gizmos", Clinical Diabetes, 2008, 26, pp. 66-71.
Citric Acid, from http://www.boldsky.com/health/nutrition/2011/natural-citric-acid-sources-030811.html, pp. 1-3, accessed Nov. 26, 2014.
DMSO Facts, from http://www.theundergroundcure.com/dmso-facts.html, p. 1, accessed Nov. 26, 2014.
Engeloch et al: "Stability of Screening Compounds in Wet DMSO", Journal of Biomolecular Screening, 2008, 13, pp. 999-1006.
Human insulin, from http://www.ncbi.nlm.nih.gov/protein/AAA59172.1, p. 1, accessed Nov. 26, 2014.
Water, from http://www.biology-online.org/dictionary/Water, pp. 1-3, accessed Apr. 24, 2014.
Hyrdochloric Acid, from http://peoplesrx.com/hyrodchloric-acid-and-the-bodys-primary-digestant/, pp. 1-2, accessed Jun. 23, 2016.
Naturally-occurring amino acids, from http://www.benjamin-mills.com/chemistry/amino-acids.htm pp. 1-5 , accessed Jun. 23, 2016.
Richards et al. "Trehalose: a review of properties, history and human tolerance, and results of multiple safety studies," *Food and Chemical Toxicology* 40: 871-898. 2002.
Notice of Reasons for Rejection issued in Japanese Application No. 2015-520527, dated May 10, 2017.
Office Action issued in Canadian Patent Application No. 2,829,400, dated Mar. 20, 2018.
Office Action issued in Chinese Patent Application No. 201610221799.6, dated May 3, 2018.
Office Action issued in Indian Patent Application No. 3948/DELNP/2014, dated Apr. 26, 2018.
Office Action issued in United Arab Emirates Patent Application No. 960/2013, dated Mar. 12, 2018.
Office Action issued in European Patent Application No. 15706976.6, dated Mar. 8, 2018.
Daiichi Sankyo, Heavy Metal Detoxicant Japanese Pharmacopoeia Dimercaprol Injection BAL Intramuscular Injection 100 mg "Daiichi Sankyo", $6^{th}$ edition, 2009, p. 1-2.
Edited by Katsuharu Kato, Medical English-Japanese Dictionary, B6 size, $11^{th}$ edition, $3^{rd}$ issue, Nanzando, 2002, p. 1082.
Eisai, Anesthesia Induction Agent, Sairesu intravenous push 2mg appended paper, $7^{th}$ edition, 2009, p. 1-3.

Extended European Search Report issued in European Application No. 17151475.5, dated Sep. 4, 2017.
Fuji Pharma, sustained Corpus Luteum Hormone formulation PROGESTON Depot Intramuscular Injection 125 mg, $4^{th}$ edition, 2009, p. 1-2.
International Preliminary Report on Patentability and Written Opinion issued in International Patent Application No. PCT/US2016/036921, dated Dec. 12, 2017.
International Preliminary Report on Patentability issued in International Application No. PCT/US2016/035792, dated Dec. 14, 2017.
International Preliminary Report on Patentability issued in International Application No. PCT/US2016/053628, dated Jan. 3, 2018.
Nanzando, Medical Dictionary (Deluxe Version), $18^{th}$ edition, $1^{st}$ issue, Nanzando, 1998, p. 1366.
Notice of Reasons for Rejection issued in Japanese Application No. 2015-520527, dated Nov. 30, 2017.
Office Action issued in Australian Application No. 2017200295, dated Nov. 30, 2017.
Office Action issued in European Application No. 15750582.7, dated Feb. 2, 2018.
Office Action issued in Indonesian Patent Application No. P-00201403186, dated Oct. 17, 2017.
Office Action issued in Israeli Application No. 228348, dated Oct. 29, 2017.
Office Action issued in Israeli Application No. 236393, dated Jul. 12, 2017.
Office Action issued in Thai Patent Application No. 140102311, dated Nov. 2, 2017.
Taiyo Yakuhin Kogyo, Minor Tranquilizer Diazepam Injection 10 mg "Taiyo" appended paper, $9^{th}$ edition, 2009, p. 1-2.
Written Opinion issued in International Application No. PCT/US2016/053628, dated Sep. 28, 2017.
Office Action issued in Japanese Patent Application No. 2017-506262, dated Mar. 4, 2019.
Office Action issued in Chinese Patent Application No. 201580018099, dated Jan. 3, 2019.
Office Action issued in United Arab Emirates Application No. 1426/2014, dated Feb. 3, 2019.
Office Action issued in corresponding Indian Patent Application No. 10985/DELNP/2014, dated Aug. 17, 2018 and received Sep. 23, 2018.
Office Action issued in corresponding Israeli Patent Application No. 236393, dated Nov. 12, 2018.
Crankshaw & Raper, "The Effect of Solvents on the Potency of Chlordiazepoxide, Diazepam, Medazepam, and Nitrazepam," *Journal of Pharmacy and Pharmacology*, 23(5): 313-321, 1971.
Office Action Issued in Corresponding Brazil Patent Application No. BR112014032695-9, dated Oct. 29, 2019.
Office Action Issued in Corresponding Korean Patent Application No. 1020157002262, dated Oct. 1, 2019.
International Search Report and Written Opinion issued in International Patent Application No. PCT/US2018/035473, dated Jul. 31, 2018.
Office Action Issued in Corresponding Chinese Patent Application No. 2017110914084, dated Jan. 19, 2020.
Search Report Issued in Corresponding Chinese Patent Application No. 2017110914084, dated Jan. 10, 2020.
Rosoff et al., "Solubilization of Diazepam in Bile Salts and in Sodium Cholate-Lecithin-Water Phases," International Journal of Pharmaceutics, 1980, Elsevier/North Holland Biomedical Press, vol. 6, Issue 2, pp. 137-146, 1980.
Shinnar et al., "Pediatric Epilepsy: Diagnosis and Therapy, Chapter 19, Febrile Seizures," 2007. 3:293-301.

* cited by examiner

STABLE FORMULATIONS FOR PARENTERAL INJECTION OF SMALL MOLECULE DRUGS

CROSS REFERENCE TO RELATED APPLICATIONS

This application is a continuation of U.S. patent application Ser. No. 13/829,937 filed Mar. 14, 2013, which claims the benefit of U.S. Provisional Application No. 61/665,021, filed Jun. 27, 2012, the entire contents of which are incorporated by reference.

BACKGROUND OF THE INVENTION

A. Field of the Invention

The present invention relates to pharmaceutical formulations and, more particularly, to pharmaceutical formulations of small molecule drugs having improved solubility and stability and to methods of using such pharmaceutical formulations to treat various diseases, conditions and disorders.

B. Description of Related Art

While many small molecule drugs are orally bioavailable, parenteral injection is also used in situations where the drug has insufficient oral bioavailability, the patient is unable to accept drugs orally, or there is a need for more rapid onset of drug action. For example, administration of benzodiazepines for emergency treatment of epileptic seizures, catecholamines for allergic reactions and "triptans" for the treatment of migraine headaches represent situations where oral administration is not as efficient or advisable and thus, the drugs must be administered via a non-oral route, often parenteral administration.

Standard practice for preparing formulations containing small molecule drugs has been to develop aqueous solutions for parenteral injection. A primary reason for this is that the majority of the human body is made up of water, including blood plasma, which is an aqueous environment. Therefore, there is a natural tendency to administer a drug formulation that is compatible with the environment that the drug is intended to reach. Several small molecule drugs, however, have limited solubility and poor stability in such aqueous environments. This has been solved, at least in part, by the use of co-solvents and stabilizers to more efficiently solubilize and stabilize the small molecule drug in a formulation.

An example of some of the difficulties associated with parenteral injection of small molecule drugs can be seen with diazepam. This drug, which is used for emergency treatment of epileptic seizures, has been hampered by its poor aqueous solubility. Thus, the currently available emergency treatment consists of a rectal gel. An attempt has also been made to develop a large-volume (up to 3 ml) intramuscular injection based on an aqueous formulation with co-solvents (larger volumes are needed due to lower solubility of diazepam). However, the development of this drug has been limited by the difficulty in delivering a deep, large volume intramuscular injection to a convulsing patient, as well as the pain associated with such a large dosage volume.

Further, due to the stability issues of small molecule drugs in aqueous environments, current products are oftentimes sold as lyophilized powders that require reconstitution in an aqueous carrier prior to injection. This allows for longer shelf-life of the drug active. Some products are even sold as liquids that require further dilution prior to injection with sterile water, phosphate buffer solution, or isotonic saline.

SUMMARY OF THE INVENTION

The present invention provides a solution to the current problems facing the use of small molecule drugs in therapeutic applications. In particular, the solution is premised on solubilizing and stabilizing a small molecule drug in a non-aqueous environment and then directly injecting the solubilized drug into a patient via parenteral administration. The formulation can be in liquid form. Once the formulation is prepared, it can be stored for an extended period of time (even in an injection device) and directly injected into a subject (e.g., human) without the reconstitution or dilution steps seen in current products. Indeed, this solution goes against the prevailing industry standard. In this regard, the inventors' solution has resulted in a more stable environment for the drug and a more efficient and effective way to actually provide life-saving drugs to those in need of treatment. Importantly, the inventors' discovery is widely applicable for the delivery of numerous small molecule drugs that, like diazepam, have poor or limited stability and solubility in an aqueous environment.

In one aspect of the present invention there is disclosed a stable liquid formulation for parenteral injection comprising a small molecule drug, or a salt thereof and a biocompatible non-aqueous solvent, wherein the small molecule drug is solubilized within the non-aqueous solvent. One of the unique aspects of the present invention is that it can be used for a wide variety of small molecule drugs, including those that currently being administered via parenteral injection. Some examples include benzodiazepines, catecholamines, and triptans. In one particular aspect, the compound is a benzodiazepine such as diazepam. The solubility of diazepam, by way of example, can be greater than what is typically seen with current products (e.g., the Examples show that diazepam solubility in DMSO can approach levels of 500 mM, which would allow for a wide range of dosaging options, such as for instance, reduced volumes of dosages—for instance, a diazepam formulation in DMSO can have 100 mM to 500 mM, 150 mM to 400 mM, 175 mM to 350 mM, or 200 mM to 300 mM of the drug, wherein each concentration provides for a substantially smaller volume to deliver the same quantity of drug compared to water-based preparations of diazepam. The Examples also show that the solubility of diazepam in NMP exceeded 700 mM, which allows for even smaller dosage volumes as needed). Other non-limiting small molecule drugs that can be used in the context of the present invention include epinephrine, sumatriptan, novantrone, chemotherapy small molecules (e.g., mitoxantrone), corticosteroid small molecules (e.g., methylprednisolone), immunosuppressive small molecules (e.g., azathioprine, cladribine, cyclophosphamide, methotrexate), anti-inflammatory small molecules (e.g., salicylic acid, acetylsalicylic acid, diflunisal, choline magnesium trisalicylate, salicylate, benorylate, flufenamic acid, mefenamic acid, meclofenamic acid, triflumic acid, diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin, sulindac, phenylbutazone, oxyphenbutazone, azapropazone, feprazone, piroxicam, isoxicam), small molecules used to treat neurological disorders (e.g., cimetidine, ranitidine, famotidine, nizatidine, tacrine, donepizil, metrifonate, rivastigmine, selegilene, imipramine, fluoxetine, olanzapine, sertindole, risperidone, valproate semisodium, gabapentin, carbamazepine, topiramate, phenytoin), and small molecules used to treat cancer (e.g., vincristine, vinblastin, paclitaxel, docetaxel, cisplatin, irinotecan, topotecan, gemcitabine, temozolomide, imatinib, bortezomib), statins (e.g., atorvastatin, amlodipine, rosuvastatin, sitagliptin, simvastatin, fluvastatin, pitavastatin, lovastatin, pravastatin, simvastatin), and other taxane derivatives. In particular embodiments, the small molecules that can be used include those that treat tuberculosis (e.g., rifampicin), small molecule anti-fungal agents (e.g., fluconazole), small molecule anti-anxiety agents and small molecule anti-convulsant agents (e.g. lorazepam), small molecule anti-cholinergic agents (e.g., atropine), small molecule f3-agonist drugs (e.g., albuterol sulfate), small molecule mast cell stabilizers and small molecule agents used to treat allergies (e.g. cromolyn sodium), small molecule anesthetic agents and small molecule anti-arrhythmic agents (e.g., lidocaine), small molecule antibiotic agents (e.g. tobramycin, ciprofloxacin), small molecule anti-migraine agents (e.g., sumatriptan), and small molecule anti-histamine drugs (e.g., diphenhydramine). Further, the amount of the small molecule drugs in the dosage formulations can be varied depending on current acceptable amounts, subject/patient needs, and the like. With respect to the biocompatible non-aqueous solvent, examples include aprotic polar solvents, alkyl or aryl benzoate solvents, lipid solvents, protic solvents, or a mixture thereof. Non-limiting examples of aprotic solvents include dimethylsulfoxide (DMSO), dimethylformamide (DMF), ethyl acetate, n-methyl pyrrolidone (NMP), dimethyl acetamide (DMA), propylene carbonate, or mixtures thereof. In some instances, however, the formulations of the present invention do not have to include the aforementioned solvents (i.e., others can be used). In one instance, for example, the formulations do not include non-aqueous aprotic polar solvents and/or do not include non-aqueous protic solvents (e.g., polyethylene glycol (PEG), propylene glycol (PG), polyvinylpyrrolidone (PVP), methoxypropylene glycol (MPEG), glycerol, glycofurol, and mixtures thereof). As noted above, the increased solubility of the small molecule drugs can result in small dosage volumes (and, in turn, small storage devices and containers), which provides for an easier and less painful administration parenterally. Non-limiting examples of aryl or alkyl benzoate solvents include methyl benzoate, ethyl benzoate, propyl benzoate, C12-C15 alkyl benzoates, in which R is a C12-15 alkyl group, C16-17 alkyl benzoate, in which R is a C16-17 fatty alcohol group, and benzyl benzoate. A non-limiting example of a lipid is triacetin, which is the triester of glycerol and acetic acid. Non-limiting examples of protic solvents include polyethylene glycol (PEG), propylene glycol (PG), polyvinylpyrrolidone (PVP), methoxypropylene glycol (MPEG), glycerol, glycofurol, or mixtures thereof. In certain aspects, the formulation does not include a co-solvent, while in other aspects it can include a co-solvent. In one instance, the formulation can include a single/only one biocompatible non-aqueous solvent (i.e., in neat or pure form). In other aspects, the formulation includes a mixture of two, three, four, or more biocompatible non-aqueous solvents. In still additional aspects, the formulation can exclude co-solvents, salts, and other ingredients that can help with or increase the solubility of the small molecule drug in the non-aqueous solvent. For instance, the formulation can consist of or consist essentially of a small molecule drug and a non-aqueous solvent (or mixture of non-aqueous solvents) and still be directly injected through parenteral administration to a subject (with consist essentially of meaning in the context of this sentence exclusion of other ingredients that could increase the solubility of the drug within the non-aqueous solvent (or mixture of non-aqueous solvents—e.g., a preservative can be included to further preserve the injectible formulation). Further, the formulation of the present invention can be non-aqueous or substantially non-aqueous (e.g., less than 10%, 9%, 8%, 7%, 6%, 5%, 4%, 3%, 2%, 1%, 0.5% or less of water by weight or volume). In some instances, the small molecule drug has previously been dried in the presence of a buffer prior to being solubilized in the non-aqueous solvent. As explained below, this can add to the stability of the small molecule drug. In some instances, the dried small molecule drug has a pH memory that is about equal to the pH of the small molecule drug in the presence of the aqueous buffer such that the pH of the small molecule drug that is solubilized in the biocompatible non-aqueous solvent is about equal to the pH of the small molecule drug in the presence of the buffer. The memory pH can be 1, 2, 3, 4, 5, 6, 7, 8, 9, 10, 11, or more or can be a range of 1 to 3, 2 to 4, 3 to 5, 4 to 6, 5 to 7, 6 to 8, 7 to 9, 8 to 10 or 9 to 11. In certain aspects, the buffer is a non-volatile buffer (non-limiting examples of which include glycine buffers, citrate buffers, or phosphate buffers, or a mixture thereof). In other instances, the buffer can be a volatile buffer. Further, the water content of the small molecule drug can be less than 5%, 4%, 3%, 2%, 1%, 0.5% or less w/w. In certain aspects, the formulation includes from 0.5 mg/mL to about 300 mg/mL, 10 mg/mL to 50 mg/mL, 20 mg/mL to 50 mg/mL, 5 mg/mL to 15 mg/mL, or 0.5 mg/mL to 2 mg/mL of the small molecule drug. In some instances, the amount of the small molecule drug can be as high as 400, 500, 600, 700, 800, 900, 1000, 2000, or 3000 mg/mL or more. One of the unique aspects of the present formulation is that the formulation can have a high content of the drug, yet the dosage amount of the formulation can be relatively low (e.g., 0.1µ, 1 µl, 10 µl, 20, µl, 50 µl, 75 µl, 100 µl, 200 µl, 300 µl, 400 µl, 500 µl, 600 µl, 700 µl, 800 µl, 900 µl, 1 ml, 2 ml, or 3 ml, or more as needed (e.g., 4, 5, 6, 7, 8, 9, 10 ml or more). In certain instances, the volume of the liquid formulation to be parenterally injected is 3 ml or less (e.g., 3, 2.5, 2, 1.5, 1, 0.5, 0.1 ml or less) or is from 0.1 µl to 3 ml or from 0.1 µl to 1 µl or from 1 µl to 10 µl or from 10 µl to 1 ml or from 0.1 µl to 2.5 ml or from 0.1 µl to 2 ml or from 0.1 µl to 1.5 ml or from 0.1 µl to 1 ml or from 0.1 µl to 0.5 ml or from 0.1 µl to 0.1 ml. Another unique aspect of the present formulation is that it can be contained in a container or device, be stored, and be immediately ready for parenteral injection on an as needed basis without having to reconstitute or dilute the formulation. The device can be a syringe, a pen injection device, an auto-injector device, a device that can pump or administer the formulation (e.g., automatic or non-automatic external pumps, implantable pumps, etc.) or a perfusion bag. Also contemplated for use in the formulations are additional ingredients/pharmaceutical excipients, non-limiting example of which include: antioxidants (examples include ascorbic acid, cysteine, methionine, monothioglycerol, sodium thiosulfate, sulfites, BHT, BHA, ascorbyl palmitate, propyl gallate, or vitamin E); chelating agents (examples include EDTA, EGTA, tartaric acid, glycerin, or citric acid); or preservatives (examples include alkyl alcohols, benzyl alcohol, a methyl paraben, or a propyl paraben or mixtures thereof). The formulation can be in liquid form, semi-solid form, or gel form. As discussed below, the formulation can have a desired viscosity range (in one non-limiting example, such a range could be between 0.5 to 15 cps). The formulation can be such that at least 65% of the small molecule drug within the formulation remains chemically and physically stable when the formulation is stored at room temperature for two months or at least 80% of the therapeutic agent within the formulation remains chemically and physically stable when the formulation is stored at room temperature for two months.

In one particular aspect of the present invention, there is disclosed a stable liquid formulation for parenteral injection comprising diazepam, or a salt thereof that has a water content of less than 1% w/w and a biocompatible non-aqueous solvent, wherein the diazepam is solubilized within the non-aqueous solvent, wherein the water content of the formulation is less than 5% w/v, wherein the volume of the formulation to be parenterally injected is between 50 µl to 1000 µl or any range therein (e.g., 75 µl, 100 µl, 150 µl, 200 µl, 300 µl, 400 µl, 500 µl, 600 µl, 700 µl, 800 µl, 900 µl, etc.). As explained above, such a formulation can be comprised in a container selected from the group con a sealed syringe, a sealed pen injection device, a sealed auto-injector device, or a pump. Also as explained above, the diazepam can be been dried in the presence of a buffer prior to being solubilized in the non-aqueous solvent. This can provide the dried diazepam with a pH memory that is about equal to the pH of diazepam in the presence of the aqueous buffer such that the pH of the diazepam that is solubilized in the biocompatible non-aqueous solvent is about equal to the pH of the diazepam in the presence of the aqueous buffer (e.g., the aforementioned non-volatile buffers such as glycine buffers, citrate buffers, or phosphate buffers, or a mixture thereof).

Also disclosed is a method of administering the formulations of the present invention by parenteral administration of the formulation to a subject in need thereof. The administration can be performed without having to reconstitute and/or dilute the formulation. Further, the administration can be performed with a syringe, a pen injection device, an auto-injector device, a pump, or a perfusion bag. Also, the formulation can be stored in said syringe, pen injection device, auto-injector device, pump, or perfusion bag, which can then be immediately used (again without having to reconstitute and/or dilute the formulation). Further, and as noted above, the amount of the formulation being administered can range from 1 µl, 10 µl, 20, µl, 50 µl, 75 µl, 100 µl, 200 µl, 300 µl, 400 µl, 500 µl, 600 µl, 700 µl, 800 µl, 900 µl, 1 ml, 2 ml, 3 ml, 4 ml, 5 ml, 6 ml, 7 ml, 8 ml, 9 ml, or 10 ml, or more as needed. In certain aspects, the formulations are such that the small molecule drug remains stable and solubilized (i.e., no coalescence or crystallization of the small molecule drug) and when stored at room temperature (approximately 20-25° C.) for at least 1, 2, 3, 4, 5, 6, 7, 8, 9, 10, 11, or 12 months.

In a further aspect of the present invention there is disclosed a method for treating or preventing a condition, disease, disorder, etc. comprising administering to a subject in need thereof any one of the formulations of the present invention in an amount effective to treat or prevent the condition, disease, disorder, etc. For instance, and with respect to the aforementioned diazepam formulation, such formulations can be used to treat epileptic seizure, especially severe seizures in an emergency situation. In this instance, the method can include administering to the subject in need thereof a soluble and stable diazepam formulation of the present invention in an amount effective to treat the seizure. The aforementioned administration techniques can be used (e.g., parenterally, pre-loaded containers, etc.). In some aspects, the condition can be anxiety, muscle spasms, or seizures (e.g., epileptic seizure).

Also contemplated is a method of the stable formulations of the present invention. The method can include obtaining a small molecule drug and adding one or more biocompatible non-aqueous solvents in an amount to sufficient dissolve the small molecule drug in the solvent. The method can further include storing the formulation in a container such as a vial or in a syringe, a pen injection device, an auto-injector device, a pump, or a perfusion bag. The process can further include drying the small molecule drug in the presence of a buffer prior to adding in the non-aqueous solvent(s). In a broader aspect, the process can be applied to formulate any small molecule drug that has limited or poor solubility or stability in an aqueous environment.

As briefly mentioned above, it is also contemplated that the viscosity of the formulations can be selected to achieve a desired result, e.g., depending on the type of composition desired, the route of administration, and the like. In one instance, the viscosity of the formulations can be from about 0.5 cps to well over 1 million cps or any range or integer derivable therein (e.g., 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc., as measured on a Brookfield Viscometer using a TC spindle at 2.5 rpm at 25° C.). In particular aspects, however, a viscosity range between 0.5 cps to about 100 cps or about 0.5 cps to about 15 cps can be used.

It is contemplated that any embodiment discussed in this specification can be implemented with respect to any method or composition of the invention, and vice versa. Furthermore, compositions of the invention can be used to achieve methods of the invention.

"Aprotic polar solvent" means a polar solvent that does not contain acidic hydrogen and does not act as a hydrogen bond donor. Examples of polar aprotic solvents include dimethylsulfoxide (DMSO), dimethylformamide (DMF), ethyl acetate, n-methyl pyrrolidone (NMP), dimethylacetamide (DMA) and propylene carbonate.

"Alkyl or aryl benzoates" refers to the following compound:

where R is an alkyl or aryl group. Examples of alkyl benzoates include methyl benzoate, ethyl benzoate, propyl benzoate, C12-C15 alkyl benzoates, in which R is a C12-15 alkyl group, and C16-17 alkyl benzoate, in which R is a C16-17 fatty alcohol group. A non-limiting example of aryl benzoate includes benzyl benzoate.

"Parenteral injection" refers to the administration of small molecule drugs via injection under or through one or more layers of skin or mucus membranes of an animal, such as a human. Standard parenteral injections are given into the subcutaneous, intramuscular, or intradermal region of an animal, e.g., a human patient. These deep locations are targeted because the tissue expands more easily, relative to shallow dermal sites, to accommodate the 0.1-3.0 cc (mL) injection volumes required to deliver most therapeutic agents.

"Pharmaceutically acceptable carrier" means a pharmaceutically acceptable solvent, suspending agent or vehicle for delivering a drug compound of the present invention to a mammal such as an animal or human.

"Pharmaceutically acceptable" ingredient, excipient or component is one that is suitable for use with humans and/or animals without undue adverse side effects (such as toxicity, irritation and allergic response) commensurate with a reasonable benefit/risk ratio.

"Chemical stability" means that with respect to the small molecule drug, an acceptable percentage of degradation products produced by chemical pathways such as oxidation or hydrolysis is formed. In particular, a formulation is considered chemically stable if no more than about 20% breakdown products are formed after one year of storage at the intended storage temperature of the product (e.g., room temperature); or storage of the product at 30° C./60% relative humidity for one year; or storage of the product at 40° C./75% relative humidity for one month, and preferably three months, and more preferably six months.

"Physical stability" means that with respect to the small molecule drug, an acceptable percentage of crystals or other aggregates (e.g., dimers, trimers, etc.) is formed. In particular, a formulation is considered physically stable if no more that about 15% aggregates are formed after one year of storage at the intended storage temperature of the product (e.g., room temperature); or storage of the product at 30° C./60% relative humidity for one year; or storage of the product at 40° C./75% relative humidity for one month, and preferably three months, and more preferably six months.

"Stable formulation" means that at least about 65% chemically and physically stable small molecule drug remains after two months of storage at room temperature. In some aspects, the formulations retain at least about 80% chemically and physically stable small molecule drug under these conditions. Even further, some stable formulations are those which do not exhibit degradation after sterilizing irradiation (e.g., gamma, beta or electron beam).

"Bioavailability" refers to the extent to which the small molecule drug is absorbed from the formulation by the subject.

"Systemic" means, with respect to delivery or administration of a small molecule drug to a subject, that therapeutic agent is detectable at a biologically significant level in the blood plasma of the subject.

"Controlled-release" refers to the release of the small molecule drug at such a rate that blood (e.g., plasma) concentrations are maintained within the therapeutic range, but below toxic concentrations over a period of time of about one hour or longer, preferably 12 hours or longer.

"Patient," "subject," or "individual" refers to a mammal (e.g., human, primate, dog, cat, bovine, ovine, porcine, equine, mouse, rate, hamster, rabbit, or guinea pig).

"Inhibiting" or "reducing" or any variation of these terms, when used in the claims and/or the specification includes any measurable decrease or complete inhibition to achieve a desired result.

"Effective" or "treating" or "preventing" or any variation of these terms, when used in the claims and/or specification, means adequate to accomplish a desired, expected, or intended result.

The term "about" or "approximately" are defined as being close to as understood by one of ordinary skill in the art, and in one non-limiting embodiment the terms are defined to be within 10%, preferably within 5%, more preferably within 1%, and most preferably within 0.5%. Further, "substantially non-aqueous" refers to less than 5%, 4%, 3%, 2%, 1%, or less by weight or volume of water.

The use of the word "a" or "an" when used in conjunction with the term "comprising" in the claims and/or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the formulations and methods disclosed in this specification includes the stability and solubility of the small molecule drugs within said formulations. Therefore, ingredients that can negatively or positively affect the stability or solubility of the small molecule drugs within the formulations would be excluded from said formulations in instances where a claim uses the transitional phrase "consisting essentially of."

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

As discussed above, the difficulties associated with formulating small molecule drugs for parenteral administration are well-documented. The current solutions to such difficulties are also well-documented and accepted as standard practice in the formulations field. Briefly, the problems begin with the desire to create aqueous formulations for small molecule drugs that would be well-tolerated and dispersible within the body (and in particular, the blood stream) despite the fact that most small molecule drugs have low solubility and stability in aqueous environments. This typically results in the use of co-solvents and drug stability agents, which can result in large and/or multiple dosages (e.g., upwards of 3 mL) to ensure that a sufficient amount of the drug is administered. Further, the added steps of reconstitution and/or dilution prior to injection can be costly and time consuming.

To address the current issues associated with parenteral administration of small molecule drugs, the inventors offer a unique approach that goes against the well-accepted and traditional formulation standards. In particular, the inventors have discovered that by solubilizing a small molecule drug in a non-aqueous environment, the resulting formulation is not only highly concentrated with the drug (which then leads to a lower dosage volume of the formulation), it also provides for increased stability and solubility of said drug. This in-turn leads to a more stable formulation that enjoys a longer shelf/storage life that can be directly injected into a subject without the use of a reconstitution or dilution step. Thus, the formulations of the present invention can be stored in a device that can immediately be used for parenteral administration.

These and other non-limiting aspects of the present invention are discussed below.

A. Small Molecule Drugs

"Small molecule drugs" in the context of the present invention are biologically active compounds (and salts thereof) that can bring about a desired, beneficial, and/or pharmacological effect on a subject. These "small molecule drugs" are organic or inorganic compounds, but they are not polymers (e.g., peptides, proteins, polypeptides, carbohydrates, and nucleic acids). Therefore, the small molecule drugs in the context of the present invention are not polymeric compounds. Typically, the small molecule drugs have a molecular weight of less than approximately 1000 Daltons. Certain small molecule drugs are "moisture sensitive" in that they are increasingly unstable in the presence of water. Also, salts that can be used with the small molecule drugs are known to those skilled in the art and include salts with inorganic acids, organic acids, inorganic bases, or organic bases.

Non-limiting examples of a few classes of small molecule drugs that can be used in the context of the present invention include benzodiazepines, catecholemines, and "triptans." As noted in the examples, one such drug diazepam, has been shown to work well in the context of the present invention as evidenced by its increased stability and solubility in a non-aqueous solvent. Other non-limiting examples include epinenpherine, sumatriptan, novantrone, chemotherapy small molecules (e.g., mitoxantrone), corticosteroid small molecules (e.g., methylprednisolone, beclomethasone dipropionate), immunosuppressive small molecules (e.g., azathioprine, cladribine, cyclophosphamide monohydrate, methotrexate), anti-inflammatory small molecules (e.g., salicylic acid, acetylsalicylic acid, diflunisal, choline magnesium trisalicylate, salicylate, benorylate, flufenamic acid, mefenamic acid, meclofenamic acid, triflumic acid, diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin, sulindac, phenylbutazone, oxyphenbutazone, azapropazone, feprazone, piroxicam, isoxicam), small molecules used to treat neurological disorders (e.g., cimetidine, ranitidine, famotidine, nizatidine, tacrine, donepizil, metrifonate, rivastigmine, selegilene, imipramine, fluoxetine, olanzapine, sertindole, risperidone, valproate semisodium, gabapentin, carbamazepine, topiramate, phenytoin), small molecules used to treat cancer (e.g., vincristine, vinblastin, paclitaxel, docetaxel, cisplatin, irinotecan, topotecan, gemcitabine, temozolomide, imatinib, bortezomib), statins (e.g., atorvastatin, amlodipine, rosuvastatin, sitagliptin, simvastatin, fluvastatin, pitavastatin, lovastatin, pravastatin, simvastatin), and other taxane derivatives, small molecules used to treat tuberculosis (e.g., rifampicin), small molecule anti-fungal agents (e.g., fluconazole), small molecule anti-anxiety agents and small molecule anti-convulsant agents (e.g., lorazepam), small molecule anti-cholinergic agents (e.g., atropine), small molecule f3-agonist drugs (e.g., albuterol sulfate), small molecule mast cell stabilizers and small molecule agents used to treat allergies (e.g., cromolyn sodium), small molecule anesthetic agents and small molecule anti-arrhythmic agents (e.g., lidocaine), small molecule antibiotic agents (e.g., tobramycin, ciprofloxacin), small molecule anti-migraine agents (e.g., sumatriptan), and small molecule anti-histamine drugs (e.g., diphenhydramine).

Each of the aforementioned drugs are well-known and commercially available from a wide variety of sources. Further, the amount of the small molecule drugs in the dosage formulations can be varied depending on current acceptable amounts, subject/patient needs (e.g., age, health, weight, nature and extend of symptom), and the like. What is unique in the context of the present invention is the fact that the dosage volumes can be decreased, and concentrated liquid preparations of the compounds can be pre-made and stored, given the increased solubility and stability of the small molecule drugs within the formulations of the present invention.

B. Biocompatible Non-Aqueous Solvents

"Biocompatible non-aqueous solvent" in the context of the present invention refers to a solvent that is substantially to completely devoid of water and is capable of solubilizing a small molecule drug. The solvent is also biocompatible in that it is suitable for use with human or animals without undue adverse side effects (such as toxicity, irritation, and allergic response) commensurate with a reasonable benefit/risk ratio.

Non-limiting examples of some suitable biocompatible, non-aqueous solvents include aprotic polar solvents, alkyl or aryl benzoates, and lipids. Examples of polar aprotic solvents include dimethylsulfoxide (DMSO), dimethylformamide (DMF), ethyl acetate, n-methyl pyrrolidone (NMP), dimethylacetamide (DMA), propylene carbonate, and mixtures thereof. Non-limiting examples of alkyl benzoates include methyl benzoate, ethyl benzoate, propyl benzoate, C12-C15 alkyl benzoates, in which R is a C12-15 alkyl group, and C16-17 alkyl benzoate, in which R is a C16-17 fatty alcohol group. A non-limiting example of aryl benzoate includes benzyl benzoate. A non-limiting example of a lipid is triacetin, which is the triester of glycerol and acetic acid.

Each of the aforementioned non-aqueous solvents are well-known and commercially available from a wide variety of sources.

C. pH Memory

In addition to the non-aqueous solvent aspect of the present invention, the inventors also discovered a further processing step that can be used to further stabilize the small molecule drug within the formulation. In particular, a small molecule drug can be mixed with a non-volatile buffer, and then dried to obtain a small molecule drug powder. Drugs are susceptible to hydrolysis at certain bonds, so the use of non-volatile buffers in the formulations of the present invention are believed to beneficially affect their chemical stability. The result of this process step is the production of a "pH memory" of the small molecule drug after it is reconstituted in then non-aqueous solvent.

In particular, the "pH memory" of small molecule drug is the resulting charge profile (protonation state) after drying the drug from a buffered aqueous solution (e.g., from a non-volatile buffer). The protonation state, and thus the solubility and stability of the drug, in very low or zero moisture non-aqueous solvents are affected by the aqueous pH of the drug solution before drying and the drying conditions employed. Similarly, the stability of uncharged drugs is impacted by pH in aqueous solutions, and thus, pH memory in a dried state or in a non-aqueous solvent. When the drug is dried in a buffer species in which both the acidic and basic components are non-volatile, the pH memory of the dried drug will be about equal to the pH of the drug in the non-volatile buffer. See, e.g., Enzymatic Reactions in Organic Media, Koskinen, A. M. P., and Klibanov, A. M., eds., Springer (1996). Furthermore, the pH of the buffered aqueous solution (e.g., non-volatile buffer) in which the drug is dried can be optimized to yield a pH memory for the drug that results in optimal drug stability, maximum solubility, and minimal degradation when the dried drug is subsequently reconstituted in the non-aqueous solvent (e.g., aprotic polar solvent). It should be noted that many non-aqueous solvents do not have exchangeable protons. Therefore, when a dried drug is reconstituted into such a solvent, the drug in the reconstituted formulation will maintain the solubility and stability characteristics of the optimal pH memory. In particular embodiments, the drug in the formulation will have a pH memory of about 2.0 to 3.0 to ensure maximal stability/minimal degradation. In other embodiments, the drug in the formulation will have a pH memory of about 3.0 to 5.0 to ensure maximal stability/minimal degradation. In yet other embodiments, the drug will have a pH memory of about 4.0 to 6.0 to ensure maximal stability/minimal degradation. In yet other embodiments, the drug will have a pH memory of about 6.0 to 11.0 to ensure maximal stability/ minimal degradation.

The pH memory of a drug can be measured in several ways. In one method, the pH memory of a drug is measured by reconstituting the dried drug into un-buffered water and measuring the pH of the reconstituted drug with a pH indicator such as pH paper or a calibrated pH electrode. Alternatively, the pH memory of a drug can be determined for a drug that has been reconstituted in a non-aqueous solvent by adding at least 20% water to the non-aqueous solvent and measuring the pH with a pH indicator. See, e.g., Baughman and Kreevoy, "Determination of Acidity in 80% Dimethyl Sulfoxide-20% Water," *Journal a/Physical Chemistry,* 78(4):421-23 (1974). Measurement of pH in an aprotic polar solvent-water solution may require a small correction (i.e., no more than 0.2 pH unit as per Baughman and Kreevoy, supra).

In view of the above, non-volatile buffers that are useful in the formulations described herein are those that are helpful in establishing a pH of maximum stability/minimal degradation as well as those that are helpful in removing residual water content from the dried drug powder. Non-volatile buffers include those buffers that will not evaporate away in a manner similar to water upon drying/lyophilization. Suitable nonvolatile buffers include, for example, glycine buffers, citrate buffers and phosphate buffers. In one preferred embodiment, the nonvolatile buffer is a glycine buffer or a citrate buffer.

In the foregoing process, drying of the drug compound with the nonvolatile buffer can be carried out using spray-drying techniques, freeze-drying techniques or lyophilization techniques. Spray drying techniques are well known to those skilled in the art. Spray drying includes the steps of atomization of a solution containing one or more solids (e.g., therapeutic agent) via a nozzle spinning disk, or other device, followed by evaporation of the solvent from the droplets. The nature of the powder that results is the function of several variables including the initial solute concentration, size distribution of droplets produced and the rate of solute removal. The particles produced may comprise aggregates of primary particles which consist of crystals and/or amorphous solids depending on the rate and conditions of solvent removal.

A spray-drying process for preparing ultra-fine powders of drugs is described, for example, in U.S. Pat. No. 6,051,256. Freeze-drying procedures are well known in the art, and are described, for example, in U.S. Pat. Nos. 4,608,764 and 4,848,094. Spray-freeze-drying processes are described, for example, in U.S. Pat. No. 5,208,998. Other spray-drying techniques are described, in U.S. Pat. Nos. 6,253,463; 6,001,336; 5,260,306; and PCT International Publication Nos. WO91/16882 and WO 96/09814.

Lyophilization techniques are well known to those skilled in the art. Basically, lyophilization is a dehydration technique that takes place while a product is in a frozen state and under a vacuum (ice sublimation under a vacuum) and drying by gentle heating. These conditions stabilize the product, and minimize oxidation and other degradative processes. The conditions of freeze drying permit running the process at low temperatures, therefore, thermally labile products can be preserved. Steps in freeze drying include pretreatment, freezing, primary drying and secondary drying. Pretreatment includes any method of treating the product prior to freezing. This may include concentrating the product, formulation revision (i.e., addition of components to increase stability and/or improve processing), decreasing a high vapor pressure solvent or increasing the surface area. Methods of pretreatment include: freeze concentration, solution phase concentration, and formulating specifically to preserve product appearance or to provide lyoprotection for reactive products, and are described, e.g., in U.S. Pat. No. 6,199,297. "Standard" lyophilization conditions, are described, e.g., in U.S. Pat. No. 5,031,336, and in "Freeze Drying of Pharmaceuticals" (DeLuca, Patrick P., J. Vac. Sci. Technol., Vol. 14, No. 1, January/February 1977); and "The Lyophilization of Pharmaceuticals: A Literature Review" (Williams, N. A., and G. P. Polli, Journal of Parenteral Science and Technology, Vol. 38, No. 2, March/April 1984).

In certain aspects, the lyophilization cycle can be partially performed above the glass transition temperature (Tg) of the therapeutic agent formulation to induce a collapse of the mass to form a dense cake containing residual water. In other embodiments, the lyophilization cycle is carried out below the glass transition temperature in order to avoid a collapse in order to achieve a complete drying of the particles.

D. Moisture Content of Formulations

An additional key aspect of the formulations of the present invention is that they have a low moisture content by virtue of using the previously described non-aqueous solvents. This provides for additional stability of both the formulation and the small molecule drug. For instance, the stable formulations of the present invention can have a moisture content that is less than 10%, 9%, 8%, 7%, 6%, 5%, 4%, 3%, 2%, 1%, 0.5%, 0.25%, 0.1%, 0.05%, 0.025%, 0.01%, to 0% by weight or volume of the formulation. In some instances, the formulation includes from about 0.01% to about 3%, from about 0.01% to about 2%, from about 0.01% to about 1.5% or from about 0.01% to about 1% by weight or volume of water in the formulation.

E. Dosages

Any suitable dosage of drugs can be administered using the formulations of the present invention. The dosage administered will, of course, vary depending upon known factors, such as: the pharmacodynamic characteristics of the particular drug, salt, or combination thereof; the age, health, or weight of the subject; the nature and extent of symptoms; the metabolic characteristics of the therapeutic agent and patient, the kind of concurrent treatment; the frequency of treatment; or the effect desired. Generally, the drug is present in the formulation in an amount ranging from about 0.5 mg/mL to about 3000 mg/mL or up to the solubility limit of the drug in the formulation. In some embodiments, the drug is present in the formulation in an amount ranging from about 10 mg/mL to about 50 mg/mL. In other embodiments, the drug is present in the formulation in an amount ranging from about 20 mg/mL to about 50 mg/mL. In still other embodiments, the drug is present in said formulation in an amount ranging from about 5 mg/mL to about 15 mg/mL. In yet other embodiments, the drug is present in the formulation in an amount ranging from about 0.5 mg/mL to about 2 mg/mL. Again, it will be readily apparent to those of skill that the drug dosage can be varied depending on the drug used and the disease, disorder or condition to be treated, and the concentration of the drug in the formulation will vary depending on the drug solubility, dosage, and method of administration.

F. Additional Ingredients/Pharmaceutical Excipients

While the formulations of the present invention are sufficient and useful with a small molecule drug and a biocompatible non-aqueous solvent (see Example 1, Tables 1-2), the formulation can include additional ingredients/pharmaceutical excipients to further develop a formula to have a desired tactile property, viscosity range, or to further protect the drug active. For instance, the formulations can further include any one of, any combination of, or all of an antioxidant (non-limiting examples of which include ascorbic acid, cysteine, methionine, monothioglycerol, sodium thiosulfate, sulfites, BHT, BHA, ascorbyl palmitate, propyl gallate, or vitamin E or any combination thereof); a chelating agent (non-limiting examples of which include EDTA, EGTA, tartaric acid and salts thereof, glycerin, and citric acid and salts thereof); and/or a preservative (non-limiting examples of which include alkyl alcohols, benzyl alcohols, methyl parabens, propyl parabens and mixtures thereof). Further, the formulations of the present invention can also include a non-aqueous protic solvent (non-limiting examples of which include polyethylene glycol (PEG), propylene glycol (PG), polyvinylpyrrolidone (PVP), methoxypropylene glycol (MPEG), glycerol, glycofurol, and mixtures thereof).

G. Kits/Containers

Kits are also contemplated as being used in certain aspects of the present invention. For instance, a formulation of the present invention can be included within a kit. A kit can include a container. In one aspect, for instance, the formulation can be comprised within a container that is ready to parenterally administer to a subject without having to reconstitute or dilute the formulation. That is, the formulation to be administered can be stored in the container and be readily used as needed. The container can be a device. The device can be a syringe, a pen injection device, an auto-injector device, a device that can pump or administer the formulation (e.g., automatic or non-automatic external pumps, implantable pumps, etc.) or a perfusion bag. Suitable pen/auto-injector devices include, but are not limited to, those pen/auto-injection devices manufactured by Becton-Dickenson, Swedish Healthcare Limited (SHL Group), YpsoMed Ag, and the like. Suitable pump devices include, but are not limited to, those pump devices manufactured by Tandem Diabetes Care, Inc., Delsys Pharmaceuticals and the like.

Alternatively, a kit of the present invention can include multiple containers or multiple compartments within a container. Each container or multiple compartments can be used to store, for instance, the biocompatible non-aqueous solvent and the small molecule drug separately. Then, as needed, the solvent and drug can be mixed together and administered immediately or stored for a later time, as needed.

EXAMPLES

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Solubility and Stability of Diazepam in Biocompatible Non-Aqueous Solvents

Diazepam, a small molecule anti-anxiety/anti-convulsant drug (MW=284.7 g/mol; anhydrous, Sigma-Aldrich, St. Louis, Mo.) powder was mixed with various biocompatible, non-aqueous solvents in 50 mg increments until it no longer dissolved. The maximum solubility of diazepam at this resolution was thus determined, and is reported in Table 1, along with the corresponding injection volume of a 20-mg dose at these concentrations.

TABLE 1

| Solvent | Solubility (mg/ml) | Solubility | Injection Volume, µl (20 mg) |
|---|---|---|---|
| NMP | 535 | Freely Soluble | 37.4 |
| DMSO | 125 | Freely Soluble | 160 |
| 70:30 DMSO:NMP | 100* | Freely Soluble | 200 |
| Benzyl benzoate | 125 | Freely Soluble | 160 |
| Triacetin | 50 | Soluble | 400 |
| PEG 300 | 50 | Soluble | 400 |

*Highest concentration tested. Based on diazepam solubility in DMSO and NMP alone, this value is expected to be at least 125 mg/ml.

Table 2 provides definitions for solubility used in Table 1 and in the following tables.

TABLE 2

| | Parts of Solvent per 1 Part Solute | Solubility Range (g/ml) | Solubility (mg/ml) |
|---|---|---|---|
| Very Soluble | <1 | >1 | >1000 |
| Freely Soluble | 1-10 | 0.1-1.0 | 100-1000 |
| Soluble | 10-30 | 0.03-0.1 | 30-100 |
| Sparingly Soluble | 30-100 | 0.01-0.03 | 10-30 |
| Slightly Soluble | 100-1000 | 0.001-0.01 | 1-10 |
| Very Slightly Soluble | 1000-10000 | 0.0001-0.001 | 0.1-1 |
| Practically Insoluble or Insoluble | >10000 | <0.0001 | <0.1 |

Diazepam solutions were prepared at various concentrations and evaluated for stability over one or six months. Solutions in Table 3 were prepared by diluting solubility test samples and were stored in glass vials at ambient conditions, and solutions in Table 4 were prepared using the following process and stored in syringes in stability chambers:

(1) Prepare any blended solvents (e.g., 70:30 DMSO:NMP) in their indicated proportions (v/v) and mix.
(2) Weigh a mass of diazepam powder appropriate for final concentration of 50 or 100 mg/mL.
(3) Dissolve diazepam powder in approximately 70% final volume solvent in glass volumetric flask fitted with ground glass stopper.

(a) Stir or sonicate solution.
(b) Requires less than 20 minutes dissolution time.
(4) Add solvent complement to bring to final solution volume.
(5) Stopper the flask and mix end-over-end at least 10 times.
(6) Verify drug content and purity via RP-HPLC.

All prepared solutions remained clear by visual inspection and no crystals were observed by light microscopy under 100× magnification in the highest concentration solutions presented in Table 3 after 10 days. Drug content and purity were evaluated using a verified USP RP-HPLC method. The absence of particulates was evaluated using visible light spectroscopy to measure transmittance at 630 nm. These data are detailed in Tables 3 and 4.

The formulations in Table 4 were placed into syringes (e.g., Daikyo Crystal Zenith syringes). To fill syringes, 500 µL of formulation was placed into syringes fitted with needle caps. A long (1½-inch) 20-gauge needle) was placed along the inner wall of the syringe barrel and the plunger was guided down into the barrel until the plunger passed the tip of the needle. This allowed air to escape without pushing the sample out of the syringe. Release testing of filled syringes was conducted to determine drug content (RP-HPLC), purity (RP-HPLC) and transmittance (at 630 nm) of the released formulation from the syringe. With the exception of two formulations, all release samples had between 100.1% and 105.2% target drug content, with at least 99.97% purity and at least 99.3% transmittance.

TABLE 3

| Solvent (Diazepam Concentration, mg/ml) | % Purity | | | % Transmittance |
|---|---|---|---|---|
| | Two Weeks | Three Weeks | One Month | One Month |
| NMP (200/100/50) | 99.73/NA/NA | 99.84/99.85/99.86 | 99.87/99.88/99.9 | NA/100/99.8 |
| DMSO (125/100/50) | 99.81/NA/NA | 99.76/99.79/99.80 | 99.8/99.83/99.85 | 99.5/NA/100 |
| Benzyl Benzoate (125/100/50) | 99.89/NA/NA | 99.88/99.90/99.85 | 99.91/99.91/99.86 | 100/99.8/100 |
| 70:30 DMSO:NMP (50) | NA | 99.78 | 99.87 | 99.5 |

TABLE 4

| Formulation Solution | Diazepam Concentration (mg/ml) | Months of Stability | 25° C./60% Relative Humidity | | | | 40° C./75% Relative Humidity | | | |
|---|---|---|---|---|---|---|---|---|---|---|
| | | | Actual Diazepam Concentration (mg/ml) | % Drug Content | % Purity | % Transmittance (630 nm) | Actual Diazepam Concentration (mg/ml) | % Drug Content | % Purity | % Transmittance |
| DMSO | 50 | T = 0 | 51.5 | 103.0% | 100.00% | 99.8 | 51.5 | 103.0% | 100.00% | 99.8 |
| | | One | 48.9 | 97.8% | 99.88% | 99.8 | 50.8 | 101.6% | 99.47% | 100.0 |
| | | Three | 50.9 | 101.7% | 100.00% | 100.0 | 49.2 | 98.3% | 100.00% | 100.0 |
| | | Six | 48.2 | 96.3% | 100.00% | 100.0 | 48.9 | 97.8% | 100.00% | 100.0 |
| | 100 | T = 0 | 102.4 | 102.4% | 100.00% | 99.8 | 102.4 | 102.4% | 100.00% | 99.8 |
| | | One | 99.6 | 99.6% | 99.86% | 100.0 | 99.2 | 99.2% | 99.63% | 100.0 |
| | | Three | 99.7 | 99.7% | 100.00% | 99.8 | 98.7 | 98.7% | 99.99% | 99.8 |
| | | Six | 98.7 | 98.7% | 100.00% | 99.8 | 81.0 | 81.0% | 100.00% | 100.0 |
| NMP | 50 | T = 0 | 51.1 | 102.1% | 99.80% | 100.0 | 51.1 | 102.1% | 99.80% | 100.0 |
| | | One | 50.4 | 100.8% | 99.97% | 100.2 | 50.9 | 101.8% | 99.95% | 100.0 |
| | | Three | 50.5 | 101.0% | 99.97% | 100.0 | 50.1 | 100.1% | 99.94% | 100.0 |
| | | Six | 50.4 | 100.8% | 99.94% | 100.0 | 101.6 | 101.6% | 99.96% | 100.0 |
| | 100 | T = 0 | 104.3 | 104.3% | 100.00% | 99.8 | 104.3 | 104.3% | 100.00% | 99.8 |
| | | One | 102.4 | 102.4% | 99.73% | 99.8 | 103.2 | 103.2% | 99.42% | 100.0 |
| | | Three | 103.1 | 103.1% | 99.98% | 99.8 | 104.0 | 104.0% | 99.96% | 99.8 |
| | | Six | 103.3 | 103.3% | 99.98% | 99.5 | 103.5 | 103.5% | 99.95% | 99.8 |
| 70 DMSO/ 30 NMP | 50 | T = 0 | 52.1 | 104.2% | 99.99% | 100.0 | 52.1 | 104.2% | 99.99% | 100.0 |
| | | One | 51.1 | 102.1% | 99.96% | 100.5 | 50.1 | 100.3% | 99.87% | 100.0 |
| | | Three | 51.4 | 102.7% | 99.99% | 100.0 | 47.8 | 95.6% | 99.99% | 99.8 |
| | | Six | 51.0 | 102.0% | 100.00% | 99.5 | 49.2 | 98.3% | 99.98% | 99.8 |
| | 100 | T = 0 | 103.6 | 103.6% | 99.99% | 100.0 | 103.6 | 103.6% | 99.99% | 100.0 |
| | | One | 101.2 | 101.2% | 99.83% | 100.5 | 102.5 | 102.5% | 99.84% | 100.7 |
| | | Three | 102.3 | 102.3% | 99.99% | 99.8 | 102.3 | 102.3% | 99.97% | 99.8 |
| | | Six | 100.8 | 100.8% | 100.00% | 99.8 | 98.7 | 98.7% | 99.97% | 99.5 |
| Benzyl Benzoate | 50 | T = 0 | 50.4 | 100.7% | 99.86% | 99.5 | 50.4 | 100.7% | 99.86% | 99.5 |
| | | One | 50.3 | 100.6% | 99.99% | 100.0 | 50.2 | 100.4% | 99.97% | 99.5 |
| | | Three | 50.8 | 101.6% | 99.97% | 100.0 | 50.5 | 100.9% | 99.96% | 100.0 |
| | | Six | 50.1 | 100.1% | 99.97% | 100.0 | 50.0 | 100.0% | 99.96% | 100.0 |
| | 100 | T = 0 | 101.8 | 101.8% | 100.00% | 99.3 | 101.8 | 101.8% | 100.00% | 99.3 |
| | | One | 100.0 | 100.0% | 99.50% | 100.0 | 100.9 | 100.9% | 99.75% | 99.5 |
| | | Three | 100.8 | 100.8% | 99.98% | 99.9 | 103.1 | 103.1% | 99.97% | 99.8 |
| | | Six | 91.2 | 91.2% | 99.97% | 99.1 | 105.5 | 105.5% | 99.98% | 99.1 |

Example 2

Pharmacokinetics of Diazepam Formulations

Figure 1:
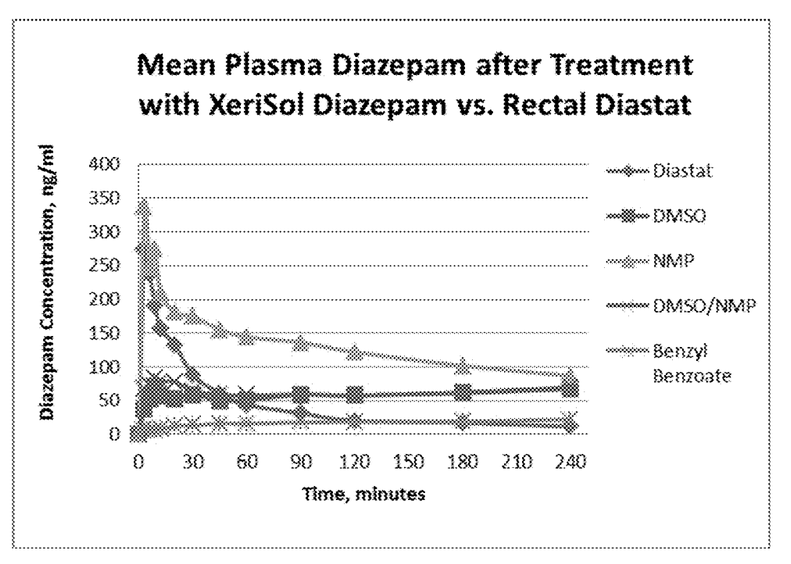
FIG. 1: Plasma diazepam levels in rats after administration of 1 mg diazepam as subcutaneous injections of Xeri-Sol™ diazepam in the indicated solvents or as Diastat rectal gel. Curves represent 5 animals per group except as otherwise noted.

A study was conducted to establish the pharmacokinetic (PK) profile in rats of four concentrated subcutaneous (SC) preparations of diazepam compared to a control formulation of rectally administered diazepam gel (Diastat, the prevailing at-home treatment for seizures)). Briefly, five jugular vein-cannulated (JVC) female Sprague-Dawley rats were dosed either by SC injection with 10 uL of liquid diazepam test article, or rectally with 200 μL of the control preparation utilizing a positive displacement pipet. Animals were fasted for 12 hours, and a small application of rectal glycerin prior to Diastat dosing were utilized to minimize defecation and expulsion of drug product in control animals. Whole blood samples were collected at 0 (pre), 3, 6, 9, 12, 20, 30, 45 minutes; 1, 1.5, 2, 3, and 4 hours post drug administration in conical tubes pre-loaded with potassium EDTA anti-coagulant. Plasma diazepam was analyzed as described below. Results are presented in FIG. 1. The preclinical study was performed at Southwest Bio-Labs (Las Cruces, N. Mex.). The study design is summarized in Table 5.

in rat plasma. Samples were frozen at the preclinical study site and shipped to ICON on dry ice. Average diazepam concentrations for all groups at nominal intervals post-administration are shown in FIG. 1.

Pharmacokinetic parameters were calculated from each individual animal and averaged by treatment group. Standard non-compartmental methods were utilized to perform calculations for $C_{max}$ (the maximum diazepam concentration), $T_{max}$ (the time that $C_{max}$ was observed, relative to dose administration), and AUC (the area under the diazepam concentration versus time curve from time 0 to 240 minutes). Additionally, the parameter $T_{1/2\ max}$ was calculated (the time at which one-half maximum concentration was observed). This parameter is useful when $C_{max}$ occurs within a broad peak or when levels around $C_{max}$ are reached quickly and then sustained, as was observed in some groups. $T_{1/2\ max}$ was derived by performing a linear regression on the initial absorption phase of the curves, and using the equation $T_{1/2\ max} = [(0.5 \times C_{max}) - (y\text{-intercept})]/\text{slope}$. Analyses of the

TABLE 5

| Group No. | Rats per Group | Test Article/ Formulation | Dose Volume (μl) | Route of Administration | Target Dose (mg/rat) | Sample Time Points* |
|---|---|---|---|---|---|---|
| 1 | 5 | Diastat Rectal Gel[a] (Control) | 200 | Rectal | 1 | 0 (pre), 3, 6, 9, 12, 20, 30, 45 minutes; 1, 1.5, 2, 3, and 4 h post-drug admin. |
| 2 | 5 | XeriSol ™ Diazepam DMSO | 10 | SC | 1 | |
| 3 | 5 | XeriSol ™ Diazepam DMSO:NMO 70:30 | 10 | SC | 1 | |
| 4 | 5 | XeriSol ™ Diazepam NMP | 10 | SC | 1 | |
| 5 | 5 | XeriSol ™ Diazepam Benzyl Benzoate | 10 | SC | 1 | |

[a]Diastat rectal gel is a non-sterile diazepam gel provided in a prefilled, unit-dose, rectal delivery system. Diastat rectal gel contains 5 mg/mL diazepam, propylene glycol, ethyl alcohol (10%), hydroxypropyl methylcellulose, sodium benzoate, benzyl alcohol (1.5%), benzoic acid and water, pH between 6.5-7.2.

There were a few noteworthy deviations from the study plan. The jugular vein cannulas presented some difficulty to study personnel and did not maintain patency throughout the study. Some blood collections were consequently delayed by a matter of minutes (each actual collection time was recorded by study personnel). Problems with the JVC caused animals in each of the XeriSol™ groups to require blood sampling from the retro-orbital sinus at various time points. One animal each in the Diastat and XeriSol™ DMSO groups were removed from the study due to complete cannula failure (prior to substituting retro-orbital bleeds). Actual collection times were used to generate individual animal time-concentration curves from which pharmacological parameters were derived.

Diazepam plasma concentrations were measured at ICON Development Solutions, LLC (Whitesboro, N.Y.). ICON used an LC/MS/MS method validated for assay of diazepam pharmacokinetic parameters were performed using SAS statistical software. Bioequivalence could not be determined due to incomplete clearance of the XeriSol diazepam formulations at the end of the study. Data are shown in Table 6.

TABLE 6

| Group | $C_{max}$, ng/mL | Area under the curve | $T_{max}$, minutes | $T_{1/2\ max}$, minutes |
|---|---|---|---|---|
| Diastat | 285.00 (44.10) | 10380 (5233) | 4.5 (1.7) | 1.9 (0.4) |
| NMP | 378.34 (467.53) | 31719 (16921) | 8.0 (4.2) | 3.6 (1.8) |
| DMSO | 89.28 (34.55) | 13936 (2591) | 129.8 (127.6) | 5.1 (3.1) |
| DMSO/NMP | 92.90 (35.20) | 14967 (5989) | 100.2 (127.6) | 3.0 (1.0) |
| Benzyl Benzoate | 22.06 (15.61) | 4093 (3332) | 204.0 (80.5) | N/A |

These data suggest that among the XeriSol™ groups, the order of effectiveness of the formulations is NMP>NMP: DMSO>DMSO>benzyl benzoate. It is clear that of the XeriSol™ formulations, NMP has the most favorable PK profile and is most comparable to the Diastat control. While all the XeriSol™ formulations, with the exception of benzyl benzoate, have increased AUC over Diastat, three of the XeriSol™ formulations fail to reach one third the $C_{max}$ of Diastat. XeriSol™ NMP, on the other hand, exceeds the Diastat $C_{max}$ by 33%. Diastat did have the shortest $T_{max}$ of all groups, but the XeriSol™ formulations raised plasma diazepam in comparably short times, again with the exception of benzyl benzoate. Whereas $T_{max}$ is large for all but XeriSol™ NMP, $T_{1/2\ max}$ demonstrates that this is an artifact of sustained concentrations of plasma diazepam near (or slightly above) a concentration that was achieved early in the time course ($T_{1/2\ max}$ was not calculated for benzyl benzoate, as $C_{max}$ was reached in only one animal; plasma diazepam continuously increased in the other four animals).

The differing $C_{max}$'s between the XeriSol™ formulations may be solubility-related, as the $C_{max}$ trend follows that of diazepam solubility in the solvents. The time to appear in the blood may be governed in part by the time required to dissolve diazepam should a precipitation event occur upon introduction to the aqueous subcutaneous environment—an event more likely with a lower solubility limit in the vehicle. This information could be useful for tailoring the PK profile through solvent combinations.

Regarding the sustained elevation of plasma diazepam in XeriSol™ groups relative to Diastat controls, differences in blood flow might be causative. From a subcutaneous injection site, diazepam presumably would enter the general circulation and have more time to accumulate in the blood vs. draining quite directly from the rectal blood supply to the liver for metabolism, as is likely the case with Diastat. This phenomenon of sustained concentrations would thus be more difficult to control. However, a sustained blood diazepam, occurring in all XeriSol™ groups throughout the duration of the study, while a measure against bioequivalence with Diastat, could prove beneficial for not only the treatment of an active seizure, but also for the prevention of follow-on or cluster seizures. This benefit would be particularly realized in the XeriSol™ NMP formulation, considered in combination with its rapid absorption profile and high $C_{max}$. Such a PK profile could also indicate that XeriSol™ diazepam may be able to attain therapeutic levels of diazepam using less drug substance per dose than Diastat.

Example 3

Solubility of Lorazepam in Biocompatible Non-Aqueous Solvents

Lorazepam, a small molecule anti-anxiety/anti-convulsant agent (MW=321.16 g/mol) was mixed with 1 gram of the following biocompatible, non-aqueous solvent in approximately 10 milligram increments until it no longer dissolved: benzyl benzoate, DMSO, NMP, Triacetin, and PEG 300. Once 50 mg of drug had been added to the solution (and the drug was still completely soluble in the solvent), the increments of drug added in each step increased to approximately 25 mg, and was maintained at approximately 25 mg until the drug no longer dissolved completely in the solution. This allowed the maximum solubility of lorazepam at this resolution to be determined for each of the five biocompatible non-aqueous solvents, as shown in Table 7.

TABLE 7

| Solvent | Solubility (mg/mL) | Solubility |
|---|---|---|
| Benzyl Benzoate | 10 | Sparingly Soluble |
| DMSO | 100 | Freely Soluble |
| NMP | 480 | Freely Soluble |
| Triacetin | 20 | Sparingly Soluble |
| PEG 300 | 80 | Soluble |

Example 4

Solubility of Albuterol Sulfate in Biocompatible Non-Aqueous Solvents

Albuterol sulfate, a small molecule immuno-suppressive/anti-cancer agent (MW=288.35 g/mol) Was mixed with the following biocompatible non-aqueous solvents (benzyl benzoate, DMSO, NMP, 70:30 (v/v) DMSO:NMP, Triacetin, and PEG 300) in amounts sufficient to prepare mixtures of increasing concentration. Specifically, the concentrations examined were 0.1 mg/mL, 1.0 mg/mL, 5 mg/mL, 10 mg/mL, 30 mg/mL, 50 mg/mL, 100 mg/mL, and increasing increments of 50 mg/mL until the small molecule drug no longer dissolved completely in the solvent. Accordingly, this allowed the maximum solubility of albuterol sulfate at this resolution to be determined for each of the six biocompatible non-aqueous solvents, as shown in Table 8.

TABLE 8

| Solvent | Solubility (mg/mL) | Solubility |
|---|---|---|
| Benzyl Benzoate | <0.1 | Practically insoluble |
| DMSO | 5 | Slightly soluble |
| NMP | <0.1 | Practically insoluble |
| 70:30 DMSO:NMP | 5 | Slightly soluble |
| Triacetin | <0.1 | Practically insoluble |
| PEG 300 | <0.1 | Practically insoluble |

Example 5

Solubility of Atropine in Biocompatible Non-Aqueous Solvents

Atropine, a small molecule anti-cholinergic agent (MW=289.4 g/mol) was mixed with the following biocompatible non-aqueous solvents (benzyl benzoate, DMSO, NMP, 70:30 (v/v) DMSO:NMP, Triacetin, and PEG 300) in amounts sufficient to prepare mixtures of increasing concentration. Specifically, the concentrations examined were 0.1 mg/mL, 1.0 mg/mL, 5 mg/mL, 10 mg/mL, 30 mg/mL, 50 mg/mL, 100 mg/mL, and increasing increments of 50 mg/mL until the small molecule drug no longer dissolved completely in the solvent. Accordingly, this allowed the maximum solubility of atropine at this resolution to be determined for each of the six biocompatible non-aqueous solvents, as shown in Table 9.

TABLE 9

| Solvent | Solubility (mg/mL) | Solubility |
|---|---|---|
| Benzyl Benzoate | 30 | Soluble |
| DMSO | 500 | Freely soluble |
| NMP | 750 | Freely soluble |
| 70:30 DMSO:NMP | 650 | Freely soluble |
| Triacetin | 5 | Slightly soluble |
| PEG 300 | 30 | Soluble |

Example 6

Solubility of Cromolyn Sodium in Biocompatible Non-Aqueous Solvents

Cromolyn sodium, a small molecule mast cell stabilizer (MW=512.3 g/mol) was mixed with the following biocompatible non-aqueous solvents (benzyl benzoate, DMSO, NMP, 70:30 (v/v) DMSO:NMP, Triacetin, and PEG 300) in amounts sufficient to prepare mixtures of increasing concentration. Specifically, the concentrations examined were 0.1 mg/mL, 1.0 mg/mL, 5 mg/mL, 10 mg/mL, 30 mg/mL, 50 mg/mL, 100 mg/mL, and increasing increments of 50 mg/mL until the small molecule drug no longer dissolved completely in the solvent. Accordingly, this allowed the maximum solubility of cromolyn sodium at this resolution to be determined for each of the six biocompatible non-aqueous solvents, as shown in Table 10.

TABLE 10

| Solvent | Solubility (mg/mL) | Solubility |
|---|---|---|
| Benzyl Benzoate | 0.1 | Very slightly soluble |
| DMSO | 50 | Soluble |
| NMP | 0.1 | Very slightly soluble |
| 70:30 DMSO:NMP | 5 | Slightly soluble |
| Triacetin | 0.1 | Very slightly soluble |
| PEG 300 | 50 | Soluble |

Example 7

Solubility of Lidocaine in Biocompatible Non-Aqueous Solvents

Lidocaine, a small molecule (MW=234.34 g/mol) was mixed with the following biocompatible non-aqueous solvents (benzyl benzoate, DMSO, NMP, 70:30 (v/v) DMSO:NMP, Triacetin, and PEG 300) in amounts sufficient to prepare mixtures of increasing concentration. Specifically, the concentrations examined were 0.1 mg/mL, 1.0 mg/mL, 5 mg/mL, 10 mg/mL, 30 mg/mL, 50 mg/mL, 100 mg/mL, and increasing increments of 50 mg/mL until the small molecule drug no longer dissolved completely in the solvent. Accordingly, this allowed the maximum solubility of lidocaine at this resolution to be determined for each of the six biocompatible non-aqueous solvents, as shown in Table 11.

TABLE 11

| Solvent | Solubility (mg/mL) | Solubility |
|---|---|---|
| Benzyl Benzoate | 900 | Freely Soluble |
| DMSO | 2000 | Very soluble |
| NMP | 1750 | Very soluble |
| 70:30 DMSO:NMP | 1750 | Very soluble |
| Triacetin | 400 | Freely soluble |
| PEG 300 | 200 | Freely soluble |

Example 8

Solubility of Rifampicin in Biocompatible Non-Aqueous Solvents

Rifampicin, a small molecule anti-tubercular agent (MW=822.94 g/mol) was mixed with the following biocompatible non-aqueous solvents (benzyl benzoate, DMSO, NMP, 70:30 (v/v) DMSO:NMP, Triacetin, and PEG 300) in amounts sufficient to prepare mixtures of increasing concentration. Specifically, the concentrations examined were 0.1 mg/mL, 1.0 mg/mL, 5 mg/mL, 10 mg/mL, 30 mg/mL, 50 mg/mL, 100 mg/mL, and increasing increments of 50 mg/mL until the small molecule drug no longer dissolved completely in the solvent. Accordingly, this allowed the maximum solubility of rifampicin at this resolution to be determined for each of the six biocompatible non-aqueous solvents, as shown in Table 12.

TABLE 12

| Solvent | Solubility (mg/mL) | Soluble |
|---|---|---|
| Benzyl Benzoate | 50 | Soluble |
| DMSO | 150 | Freely soluble |
| NMP | 400 | Freely soluble |
| 70:30 DMSO:NMP | 150 | Freely soluble |
| Triacetin | 5 | Slightly soluble |
| PEG 300 | 5 | Slightly soluble |

Example 9

Solubility of Epinephrine Bitartrate in Biocompatible Non-Aqueous Solvents

Epinephrine bitartrate, a small molecule sympathomimetic (MW=333.3 g/mol) was mixed with the following biocompatible non-aqueous solvents (benzyl benzoate, DMSO, NMP, 70:30 (v/v) DMSO:NMP, Triacetin, and PEG 300) in amounts sufficient to prepare mixtures of increasing concentration. Specifically, the concentrations examined were 0.1 mg/mL, 1.0 mg/mL, 5 mg/mL, 10 mg/mL, 30 mg/mL, 50 mg/mL, 100 mg/mL, and increasing increments of 50 mg/mL until the small molecule drug no longer dissolved completely in the solvent. Accordingly, this allowed the maximum solubility of epinephrine bitartrate at this resolution to be determined for each of the six biocompatible non-aqueous solvents, as shown in Table 13.

TABLE 13

| Solvent | Solubility (mg/mL) | Solubility |
|---|---|---|
| Benzyl Benzoate | <0.1 | Practically insoluble |
| DMSO | 700 | Freely soluble |
| NMP | 400 | Freely soluble |
| 70:30 DMSO:NMP | 500 | Freely soluble |
| Triacetin | <0.1 | Practically insoluble |
| PEG 300 | 0.1 | Very slightly soluble |

Example 10

Solubility of Acetylsalicylic Acid in Biocompatible Non-Aqueous Solvents

Acetylsalicylic acid, a small molecule analgesic agent (MW=180.16 g/mol) was mixed with the following biocompatible non-aqueous solvents (benzyl benzoate, DMSO, NMP, 70:30 (v/v) DMSO:NMP, Triacetin, and PEG 300) in amounts sufficient to prepare mixtures of increasing concentration. Specifically, the concentrations examined were 0.1 mg/mL, 1.0 mg/mL, 5 mg/mL, 10 mg/mL, 30 mg/mL, 50 mg/mL, 100 mg/mL, and increasing increments of 50 mg/mL until the small molecule drug no longer dissolved completely in the solvent. Accordingly, this allowed the maximum solubility of acetylsalicylic acid at this resolution to be determined for each of the six biocompatible non-aqueous solvents, as shown in Table 14.

TABLE 14

| Solvent | Solubility (mg/mL) | Solubility |
|---|---|---|
| Benzyl Benzoate | 30 | Soluble |
| DMSO | 2000 | Very soluble |

TABLE 14-continued

| Solvent | Solubility (mg/mL) | Solubility |
|---|---|---|
| NMP | 1200 | Very soluble |
| 70:30 DMSO:NMP | 1450 | Very soluble |
| Triacetin | 5 | Slightly soluble |
| PEG 300 | 5 | Slightly soluble |

Example 11

Solubility of Beclomethasone Dipropionate in Biocompatible Non-Aqueous Solvents Beclomethasone dipropionate, a small molecule corticosteroid (MW=521.04 g/mol) was mixed with the following biocompatible non-aqueous solvents (benzyl benzoate, DMSO, NMP, 70:30 (v/v) DMSO:NMP, Triacetin, and PEG 300) in amounts sufficient to prepare mixtures of increasing concentration. Specifically, the concentrations examined were 0.1 mg/mL, 1.0 mg/mL, 5 mg/mL, 10 mg/mL, 30 mg/mL, 50 mg/mL, 100 mg/mL, and increasing increments of 50 mg/mL until the small molecule drug no longer dissolved completely in the solvent. Accordingly, this allowed the maximum solubility of beclomethasone dipropionate at this resolution to be determined for each of the six biocompatible non-aqueous solvents, as shown in Table 15.

TABLE 15

| Solvent | Solubility (mg/mL) | Soluble |
|---|---|---|
| Benzyl Benzoate | 50 | Soluble |
| DMSO | 1700 | Very soluble |
| NMP | 1800 | Very soluble |
| 70:30 DMSO:NMP | 1700 | Very soluble |
| Triacetin | 5 | Slightly soluble |
| PEG 300 | 30 | Soluble |

Example 12

Solubility of Sumatriptan Succinate in Biocompatible Non-Aqueous Solvents

Sumatriptan succinate, a small molecule anti-migraine drug (MW=413.49 g/mol) was mixed with the following biocompatible non-aqueous solvents (benzyl benzoate, DMSO, NMP, 70:30 (v/v) DMSO:NMP, Triacetin, and PEG 300) in amounts sufficient to prepare mixtures of increasing concentration. Specifically, the concentrations examined were 0.1 mg/mL, 1.0 mg/mL, 5 mg/mL, 10 mg/mL, 30 mg/mL, 50 mg/mL, 100 mg/mL, and increasing increments of 50 mg/mL until the small molecule drug no longer dissolved completely in the solvent. Accordingly, this allowed the maximum solubility of sumatriptan succinate at this resolution to be determined for each of the six biocompatible non-aqueous solvents, as shown in Table 16.

TABLE 16

| Solvent | Solubility (mg/mL) | Soluble |
|---|---|---|
| Benzyl Benzoate | <0.1 | Practically insoluble |
| DMSO | 350 | Freely soluble |
| NMP | 100 | Freely soluble |
| 70:30 DMSO:NMP | 300 | Freely soluble |
| Triacetin | <0.1 | Practically insoluble |
| PEG 300 | 0.1 | Very slightly soluble |

Example 13

Solubility of Diphenhydramine Hydrochloride in Biocompatible Non-Aqueous Solvents Diphenhydramine hydrochloride, a small molecule antihistamine drug (MW=291.82 g/mol) was mixed with the following biocompatible non-aqueous solvents (benzyl benzoate, DMSO, NMP, 70:30 (v/v) DMSO:NMP, Triacetin, and PEG 300) in amounts sufficient to prepare mixtures of increasing concentration. Specifically, the concentrations examined were 0.1 mg/mL, 1.0 mg/mL, 5 mg/mL, 10 mg/mL, 30 mg/mL, 50 mg/mL, 100 mg/mL, and increasing increments of 50 mg/mL until the small molecule drug no longer dissolved completely in the solvent. Accordingly, this allowed the maximum solubility of diphenhydramine hydrochloride at this resolution to be determined for each of the six biocompatible non-aqueous solvents, as shown in Table 17.

TABLE 17

| Solvent | Solubility (mg/mL) | Soluble |
|---|---|---|
| Benzyl Benzoate | 0.1 | Very slightly soluble |
| DMSO | 300 | Freely soluble |
| NMP | 100 | Freely soluble |
| 70:30 DMSO:NMP | 150 | Freely soluble |
| Triacetin | 0.1 | Very slightly soluble |
| PEG 300 | 50 | Soluble |

Example 14

Solubility of Fluconazole in Biocompatible Non-Aqueous Solvents

Fluconazole, a small molecule anti-fungal drug (MW=306.27 g/mol) was mixed with the following biocompatible non-aqueous solvents (benzyl benzoate, DMSO, NMP, 70:30 (v/v) DMSO:NMP, Triacetin, and PEG 300) in amounts sufficient to prepare mixtures of increasing concentration. Specifically, the concentrations examined were 0.1 mg/mL, 1.0 mg/mL, 5 mg/mL, 10 mg/mL, 30 mg/mL, 50 mg/mL, 100 mg/mL, and increasing increments of 50 mg/mL until the small molecule drug no longer dissolved completely in the solvent. Accordingly, this allowed the maximum solubility of fluconazole at this resolution to be determined for each of the six biocompatible non-aqueous solvents, as shown in Table 18.

TABLE 18

| Solvent | Solubility (mg/mL) | Solubility |
|---|---|---|
| Benzyl Benzoate | 5 | Slightly soluble |
| DMSO | 900 | Freely soluble |
| NMP | 800 | Freely soluble |
| 70:30 DMSO:NMP | 850 | Freely soluble |
| Triacetin | 5 | Slightly soluble |
| PEG 300 | 50 | Soluble |

Example 15

Solubility of Tobramycin in Biocompatible Non-Aqueous Solvents

Tobramycin, a small molecule aminoglycoside antibiotic (MW=467.51 g/mol) was mixed with the following biocompatible non-aqueous solvents (benzyl benzoate, DMSO, NMP, 70:30 (v/v) DMSO:NMP, Triacetin, and PEG 300) in amounts sufficient to prepare mixtures of increasing concentration. Specifically, the concentrations examined were 0.1 mg/mL, 1.0 mg/mL, 5 mg/mL, 10 mg/mL, 30 mg/mL, 50 mg/mL, 100 mg/mL, and increasing increments of 50 mg/mL until the small molecule drug no longer dissolved completely in the solvent completely in the solvent. Accordingly, this allowed the maximum solubility of tobramycin at this resolution to be determined for each of the six biocompatible non-aqueous solvents, as shown in Table 19.

TABLE 19

| Solvent | Solubility (mg/mL) | Solubility |
|---|---|---|
| Benzyl Benzoate | <0.1 | Practically insoluble |
| DMSO | <0.1 | Practically insoluble |
| NMP | <0.1 | Practically insoluble |
| 70:30 DMSO:NMP | <0.1 | Practically insoluble |
| Triacetin | 0.1 | Very slightly soluble |
| PEG 300 | 0.1 | Very slightly soluble |

Example 16

Solubility of Cyclophosphamide Monohydrate in Biocompatible Non-Aqueous Solvents Cyclophosphamide monohydrate, a small molecule immuno-suppressive/anti-cancer agent (MW=279.10 g/mol) was mixed with the following biocompatible non-aqueous solvents (benzyl benzoate, DMSO, NMP, 70:30 (v/v) DMSO:NMP, Triacetin, and PEG 300) in amounts sufficient to prepare mixtures of increasing concentration. Specifically, the concentrations examined were 0.1 mg/mL, 1.0 mg/mL, 5 mg/mL, 10 mg/mL, 30 mg/mL, 50 mg/mL, 100 mg/mL, and increasing increments of 50 mg/mL until the small molecule drug no longer dissolved completely in the solvent. Accordingly, this allowed the maximum solubility of cyclophosphamide monohydrate at this resolution to be determined for each of the six biocompatible non-aqueous solvents, as shown in Table 20.

TABLE 20

| Solvent | Solubility (mg/mL) | Soluble |
|---|---|---|
| Benzyl Benzoate | 100 | Freely soluble |
| DMSO | 2800 | Very soluble |
| NMP | 2100 | Very soluble |
| 70:30 DMSO:NMP | 2700 | Very soluble |
| Triacetin | 150 | Freely soluble |
| PEG 300 | 100 | Freely soluble |

All of the ingredients, compositions, or methods disclosed and claimed in this specification can be made and executed without undue experimentation in light of the present disclosure. While the ingredients, compositions, or methods of this invention have been described in terms of particular embodiments, it will be apparent to those of skill in the art that variations may be applied to the active ingredients, compositions, or methods and in the steps or in the sequence of steps of the method described herein without departing from the concept, spirit and scope of the invention.

The invention claimed is:

1. A parenteral injection device comprising:
   an injection device containing an injectable composition comprising:
   (a) a dimethylsulfoxide (DMSO) solvent; and
   (b) a benzodiazepine, or a salt thereof, solubilized within the solvent, wherein the benzodiazepine is present in the injectable composition in an amount up to its solubility limit, wherein the benzodiazepine consists of diazepam,
   wherein the injectable composition comprises less than 5% by weight residual water, and the volume of the injectable composition to be parenterally injected is 3 ml or less.

2. The injection device of claim 1, wherein the injection device is a syringe, a pen injection device, an auto-injector device, an external or implantable pump, or a perfusion bag.

3. The injection device of claim 1, wherein the injectable composition comprises 50 mg/ml to 300 mg/ml of diazepam.

4. The injection device of claim 1, wherein the volume of the injectable composition to be parenterally injected is from 0.1 µl to 1 µl.

5. The injection device of claim 1, wherein the volume of the injectable composition to be parenterally injected is from 1 µl to 10 µl.

6. The injection device of claim 1, wherein the volume of the injectable composition to be parenterally injected is from 10 µl to 1 ml.

7. The injection device of claim 1, wherein the volume of the injectable composition to be parenterally injected is from 1 ml to 3 ml.

8. A method of using the injection device of claim 1 to a subject, the method comprising parenterally injecting the injectable composition to the subject.

9. The method of claim 8, wherein the injectable composition is parenterally injected with a syringe, a pen injection device, an auto-injector device, an external or implantable pump, or a perfusion bag.

10. The method of claim 8, wherein the injectable composition is not diluted prior to administration.

11. A method of treating anxiety, muscle spasms, or seizures, the method comprising parenterally injecting the injectable composition using the injection device of claim 1 to a subject in need thereof.

12. The method of claim 11, wherein the injectable composition is parenterally injected with a syringe, a pen injection device, an auto-injector device, an external or implantable pump, or a perfusion bag.

13. The method of claim 11, wherein the injectable composition is not diluted prior to administration.

* * * * *